(12) United States Patent
Georg et al.

(10) Patent No.: US 9,150,600 B2
(45) Date of Patent: Oct. 6, 2015

(54) TRIPTOLIDE PRODRUGS

(71) Applicant: REGENTS OF THE UNIVERSITY OF MINNESOTA, St. Paul, MN (US)

(72) Inventors: Ingrid Gunda Georg, St. Paul, MN (US); Satish Prakash Patil, St. Paul, MN (US); Ashok K. Saluja, St. Paul, MN (US); Rohit Chugh, St. Paul, MN (US); Selwyn M. Vickers, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 13/938,971

(22) Filed: Jul. 10, 2013

(65) Prior Publication Data

US 2014/0107077 A1 Apr. 17, 2014

Related U.S. Application Data

(62) Division of application No. 13/319,316, filed as application No. PCT/US2010/034117 on May 7, 2010, now Pat. No. 8,507,552.

(60) Provisional application No. 61/176,249, filed on May 7, 2009.

(51) Int. Cl.
| A61K 31/343 | (2006.01) |
| C07F 9/06 | (2006.01) |
| C07F 9/6561 | (2006.01) |

(52) U.S. Cl.
CPC .................................. C07F 9/6561 (2013.01)

(58) Field of Classification Search
CPC ................................ A61K 31/343; C07F 9/06
USPC ................... 549/218, 220; 514/449, 461, 468
See application file for complete search history.

(56) References Cited

U.S. PATENT DOCUMENTS

| 5,698,376 | A | 12/1997 | Briguglio et al. |
| 5,759,550 | A | 6/1998 | Wiedmann et al. |
| 5,843,452 | A | 12/1998 | Wiedmann et al. |
| 5,962,516 | A | 10/1999 | Qi et al. |
| 6,150,539 | A | 11/2000 | Musser |
| 6,548,537 | B1 | 4/2003 | Dai et al. |
| 6,569,893 | B2 | 5/2003 | Dai et al. |
| 6,620,843 | B2 | 9/2003 | Fidler et al. |
| 7,662,976 | B2 | 2/2010 | Dai et al. |
| 8,507,552 | B2 | 8/2013 | Georg et al. |
| 2003/0206861 | A1 | 11/2003 | Rosen et al. |
| 2004/0235943 | A1 | 11/2004 | Dai et al. |
| 2005/0288364 | A1 | 12/2005 | Dai et al. |
| 2006/0111327 | A1 | 5/2006 | Wang et al. |
| 2006/0128975 | A1 | 6/2006 | Dai et al. |
| 2007/0244080 | A1 | 10/2007 | Fidler et al. |
| 2007/0249048 | A1 | 10/2007 | Dai et al. |

FOREIGN PATENT DOCUMENTS

| CN | 1483731 A | 3/2004 |
| EP | 1552829 A1 | 7/2005 |
| JP | 2002-522443 | 7/2002 |
| JP | 2005-514431 | 5/2005 |
| JP | 2005-187422 A | 7/2005 |
| JP | 2006503831 A | 2/2006 |
| WO | WO 97/31920 A1 | 9/1997 |
| WO | WO 00/12483 A1 | 3/2000 |
| WO | WO 00/48619 A1 | 8/2000 |
| WO | WO 00/63212 A1 | 10/2000 |
| WO | WO 01/15707 A1 | 3/2001 |
| WO | WO 02/056835 A2 | 7/2002 |
| WO | WO 02/070472 A2 | 9/2002 |
| WO | WO 02/074759 A1 | 9/2002 |
| WO | WO 03/101951 A2 | 12/2003 |
| WO | WO 2004/058770 A1 | 7/2004 |
| WO | WO 2005/020887 A2 | 3/2005 |
| WO | WO 2005/062913 A2 | 7/2005 |
| WO | WO 2005/084365 A2 | 9/2005 |

(Continued)

OTHER PUBLICATIONS

Aghdassi et al., "Heat shock protein 70 increases tumorigenicity and inhibits apoptosis in pancreatic adenocarcinoma", *Cancer Research*, 67(2), 616-625 (2007).
Antonoff et al., "Triptolide therapy for neuroblastoma decreases cell viability in vitro and inhibits tumor growth in vivo", *Surgery*, 146, 282-290 (2009).
Antonoff et al., "Association for Academic Surgery; Role of Hsp-70 in Triptolide-Mediated Cell Death of Neuroblastoma", *Journal of Surgical Research*, 163, 72-78, (2010).
Aoyagi et al., "Semisynthesis of C-ring modified triptolide analogues and their cytotoxic activities", *Bioorganic & Medicinal Chemistry Letters*, 16, 1947-1949 (2006).
Banerjee et al., "Minnelide reducs tumor burden in preclinical models of osteosarcoma", Article in Press: *Cancer Letters*, 9 pages (Mar. 16, 2013).

(Continued)

*Primary Examiner* — Golam M M Shameem
(74) *Attorney, Agent, or Firm* — Viksnins Harris & Padys PLLP

(57) ABSTRACT

The invention provides compounds of formula I:

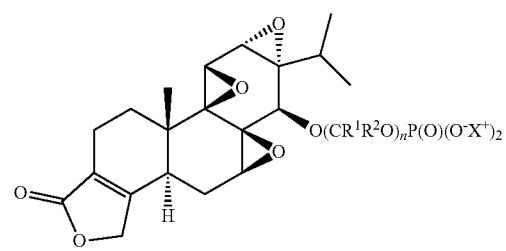

or a salt thereof. The invention also provides pharmaceutical compositions comprising a compound of formula I, processes for preparing compounds of formula I, intermediates useful for preparing compounds of formula I and therapeutic methods using the compounds of formula I.

21 Claims, 20 Drawing Sheets

(56) References Cited

FOREIGN PATENT DOCUMENTS

| WO | WO 2006/012204 A2 | 2/2006 |
|---|---|---|
| WO | WO 2007/025031 A2 | 3/2007 |
| WO | WO 2007/112648 A1 | 10/2007 |
| WO | WO 2008/014602 A1 | 2/2008 |
| WO | WO 2008/108384 A1 | 9/2008 |
| WO | WO 2009/016269 A1 | 2/2009 |
| WO | WO 2009/023201 A1 | 2/2009 |

OTHER PUBLICATIONS

Borja-Cacho et al., "TRAIL and Triptolide: An Effective Combination that Induces Apoptosis in Pancreatic Cancer Cells", *J. Gastrointest Surg*, 14, 252-260 (2010).

Chassaing et al., "Highly Water-Soluble Prodrugs of Anthelminthic Benzimidazole Carbamates: Synthesis, Pharmacodynamics and Pharmacokinetics", *J. Med. Chem.*, 51(5), 1111-1114 (2008).

Chugh et al., "Therapeutic Management of Pancreatic Cancer Using a Novel Drug, Minnelide", Abstract of papers, 101st Annual AACR Meeting, Washington, DC, Abstract #1771, 2 pages (Apr. 19, 2010).

Chugh, et al., "Minnelide as an Emerging Single Therapeutic Agents Against Pancreatic Cancer", *Gastroenterology*, 138 (5), (2012), Supplement 1, S-80, May 1-5, 2010, American Gastroenterology Association (AGA) meeting, New Orleans, abstract #570.

Chugh et al., "A Preclinical Evaluation of Minnelide as a Therapeutic Agent Against Pancreatic Cancer", *Sci Transl Med.*, 4(156), 156ra139, 1-10 (2012).

Clawson et al., "Association for Academic Surgery, Triptolide and TRAIL Combination Enhances Apoptosis in Cholangiocarcinoma", *Journal of Surgical Research*, 163, 244-249 (2010).

D'Cunha et al., "Minnelide Decreases Tumor Growth in non-Small Cell Lung Carcinoma", 6$^{th}$ Annual Academic Surgical Congress, Huntington Beach, CA, 2 pages (Feb. 1-3, 2011).

Degoey et al., "Water-Soluble Prodrugs of the Human Immunodeficiency Virus Protease Inhibitors Lopinavir and Ritonavir", *J. Med. Chem.*, 52 (9), 2964-2970 (2009).

Dudeja et al., "Heat Shock Protein 70 Inhibits Apoptosis in Cancer Cells Through Simultaneous and Independent Mechanisms", *Gastroenterolgy*, 136, 1772-1782 (2009).

Dudeja et al., "Triptolide: A Novel Therpeutic Strategy for Colorectal Cancer", Presenation at American College of Surgeons Meeting, 1 page (2011).

Dudeja et al., "Effect of *Minnelide* on Colon Cancer Metastasis", Presentation at 97$^{th}$ Annual American College of Surgeons Clinical Congress, San Francisco, CA, 2 pages (Oct. 23-27, 2011).

Fuqua et al., "Heat Shock Proteins and Drug Resistance," *Breast Cancer Res. Treatment*, 32, 67-71 (1994).

Georg, et al., "Natural Products as Promising Therapeutics for Pancreatic Cancer Treatment", American Society of Pharmacognosy and Phytochemical Society of North America Meeting. St. Petersburg Beach, FL., Paper 4060, abstract 2839 (Jul. 10-14, 2010).

Hantschel et al., "Hsp70 plasma membrane expression on primary tumor biopsy material and bone marrow of leukemic patients," *Cell Stress Chaperones*, 5 (5), 438-442 (2000).

Harrousseau et al., "Phase I Study of F60008, a Triptolide Derivative, in Patients with Refractory or Relapsing Acute Leukemias", *Haematologica*, 93(s1), 14, Abstract 0038 (2008).

He et al., Triptolide functions as a potent angiogenesis inhibitor, *Int. Journal of Cancer*, 126, 266-278 (2010).

Hingorani et al., "Pancreas Cancer Meets the Thunder God", *Science Translation Medicine*, vol. 4, Issue 15, 1-4 (2012).

Isharwal et al., "Triptolide: A Novel Therapeutic Strategy for Prostate Cancer", Presented at American Urological Associateion Annual Meeting, Washington D.C., 1 page (May 2011).

Isharwal et al., "Minnelide Induces Prostate Cancer Cell Death in an in-vivo Model", Presentation at American Urological Associate Annual Scientific Meeting, Washington D.C., 2 pages (May 14-19, 2011).

Kitzen et al., "Phase I dose-escalation study of F60008, a novel apoptosis inducer, in patients with advanced solid tumours," *European Journal of Cancer*,45, 1764-1772 (2009).

Krise et al., "Novel Prodrug Approach for Tertiary Amines: Synthesis and Preliminary Evaluation of N-Phosphonooxymethyl Prodrugs," *J. Med. Chem.*, 42, 3094-3100 (1999).

Krosch et al., "Triptolide-mediated cell death in neuroblastoma occurs by both apoptosis and autophagy pathways and results in inhibition of nuclear factor-kappa B activity", *The American Journal Surgery*, 205, 387-396 (2013).

Kumpulainen et al., "Synthesis, in vitro and in vivo characterization of novel ethyl dioxy phosphate prodrug of propofol", *European Journal of Pharmaceutical Sciences*, 34, 110-117 (2008).

Li et al., "Design and Synthesis of Novel C14-Hydroxyl Substituted Triptolide Derivatives as Potential Selective Antitumor Agents", *J. Med. Chem.*, 52, 5115-5123 (2009).

Lin et al., "Minnelide Decreases Tumor Growth in a Patient Derived Tumor Xenograft of Head and Neck Carcinoma", Presented at American Head and Neck Society Meeting (COSM), 2 pages (2012).

Mujumdar et al., "Autophagy in pancreatic cancer; An emerging mechanism of cell death", *Autophagy*, 6 (7), 997-998 (2010).

Mujumdar et al., "Triptolide Induces Cel Death in Pancreatic Cancer Cells by Apoptotic and Autophagic Pathways", *Gastroenterology*, 139, 598-608 (2010).

Patent Cooperation Treaty, International Searching Authority, Search Report and Written Opinion for PCT/US2010/034117, 12 pages, dated Jul. 26, 2010.

Patil, Satish P., Ph.D. "Preclinical Development of a Novel Triptolide Prodrug for Cancer Treatment", Dissertation submitted to the Faculty of Graduate School of the University of Minnesota, 166 pages (Jan. 2011).

Phillips et al., "Triptolide induces pancreatic cancer cell death via inhibition of heat shock protein 70," *Cancer Research*, 67(19), 9407-9416 (2007).

Qiu et al., "Immunosuppressive and Anti-Inflammatory Mechanisms of Triptolide, the Principal Active Diterpenoid from the Chinese Medicinal Herb *Tripterygium wilfordii* Hook. F.", *Drugs R.D.* 4 (1), 1-18 (2003).

Saluja et al., "Cell Death and Survival; Heat shock proteins in pancreatic diseases", *Journal of Gastroenterology and Hepatology*, 23, Suppl. 1, S42-S45 (2008).

Saluja, "Minnelide™: A Novel Therapy for Pancreatic Cancer", Presentation at University of Minnesota, Twin Cities Campus, 75 pages (2010).

Saluja "Minnelide: A Novel Therapy for Pancreatic Cancer" Presentation at University of Minnesota, Twin Cities Campus, PACA Awareness, 29 pages, Nov. 29, 2011.

Wang et al., "Enhanced anti-tumor effect via combination of Triptolide with ionizing radiation", *Proc. Amer. Assoc. Cancer Res.*, 47, Abstract #4720 (2006).

Wang et al., "Mechanism of triptolide-induced apoptosis: effect on caspase activation and Bid cleavage and essentiality of the hydroxyl group of triptolide", *Journal of Molecular Medicine*, 84, 405-415 (2006).

Wang et al., "Enhanced Antitumor Effect of Combined Triptolide and Ionizing Radiation", *Clin. Cancer Res.*, 13 (16), 4891-4899 (2007).

Westerheide et al., "Triptolide, an Inhibitor of the Human Heat Shock Response that Enhances Stress-induced Cell death", *Journal of Biological Chemistry*, 281 (14), 9616-9622 (2006).

Xu et al., "Design, synthesis, and biological evaluation of novel water-soluble triptolide derivatives: Antineoplastic activity against imatinib-resistant CML cells bearing T3151 mutant Bcr-Abl", *Bioorganic & Medicinal Chemistry*, 18, 1806-1815 (2010).

Yang et al., "Triptolide Inhibits the Growth and Metastasis of Solid Tumors", *Mol. Cancer Ther.*, 2, 65-72 (2003).

Figure 13. Survival analysis of Compound 1 treated or control mice.
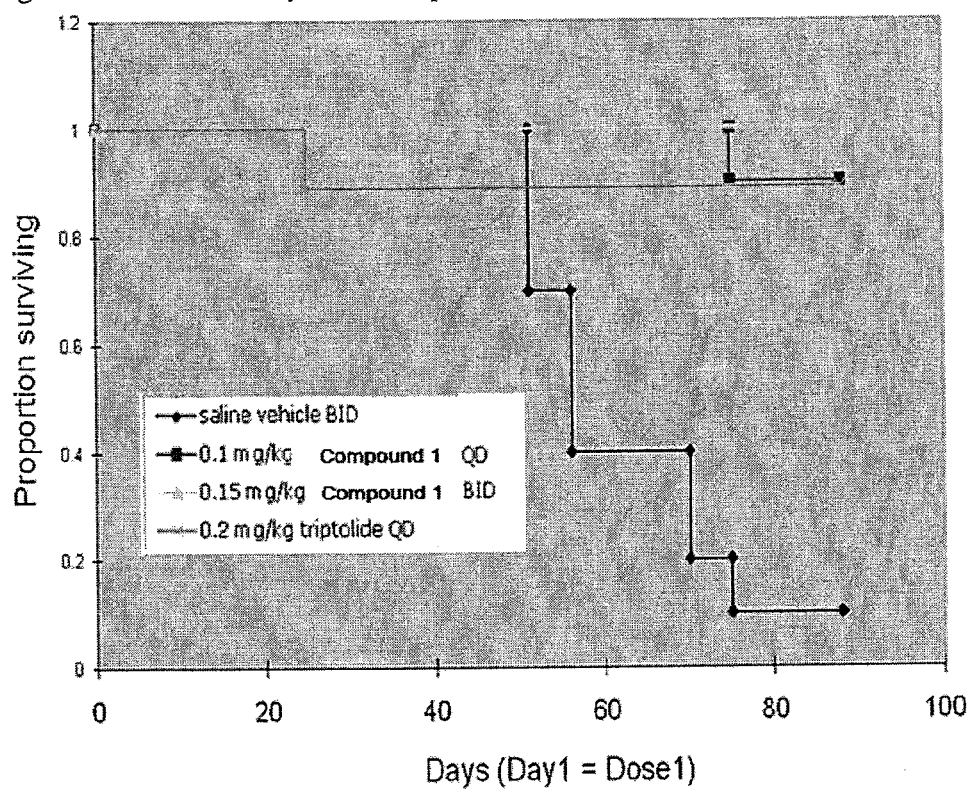
Vehicle BID: All deaths were from tumor burden
0.1mg/kg Compound 1 QD: 1 observed death is from tumor burden
0.15mg/kg Compound 1 BID: no deaths
0.2mg/kg Compound 1 QD: 1 death is from injury, not related to tumor burden or drug effect.

Figure 14. Survival analysis of Compound 1 treated or control mice.
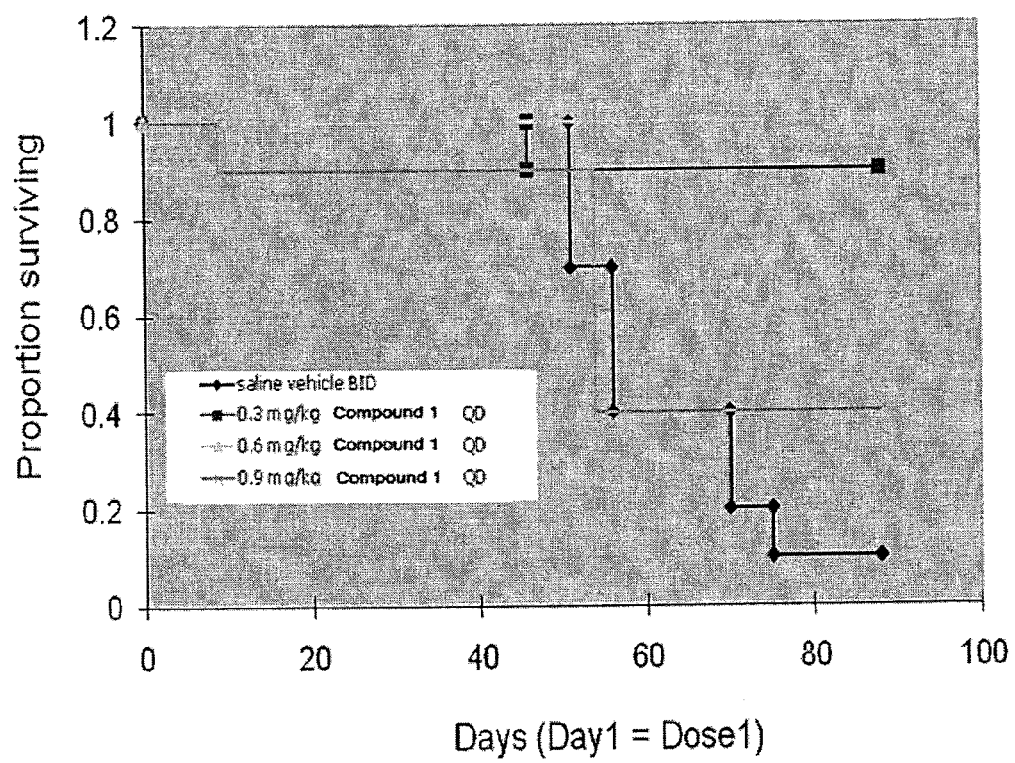
Vehicle BID: All deaths were from tumor burden
0.3mg/kg Compound 1 QD: 1 death is from injury not related to tumor burden
0.6mg/kg Compound 1 QD: no deaths
0.9mg/kg Compound 1 QD: 1 death at injection on study day6, cause undetermined. Remaining deaths are from drug effect.

Figure 15. Tumor burden (volume or weight) analysis of Compound 1 treated or control mice.
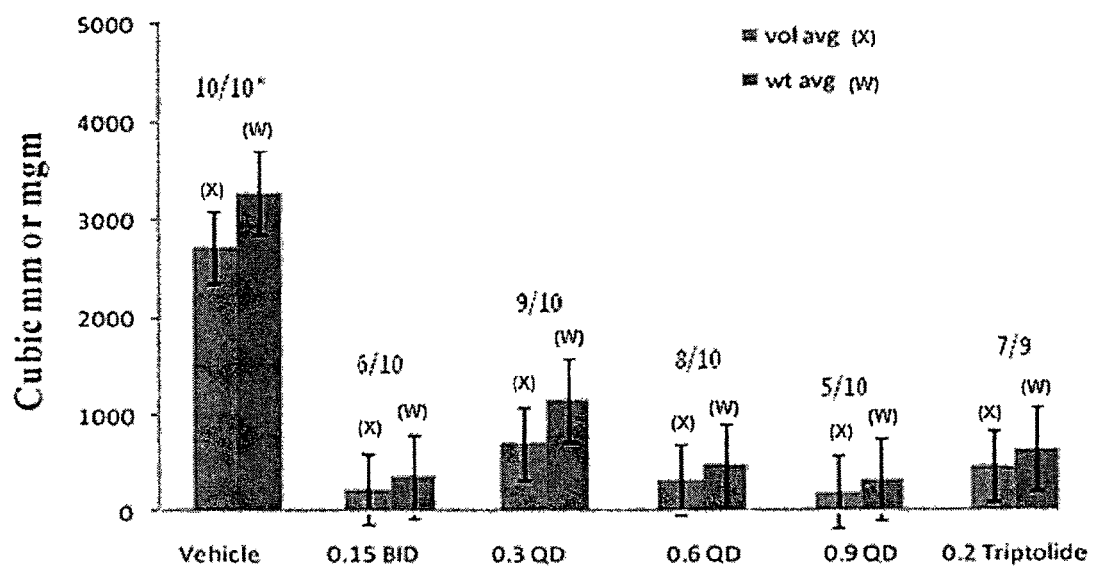

Figure 16. Tumor burden (volume or weight) analysis of Compound 1 treated or control mice.
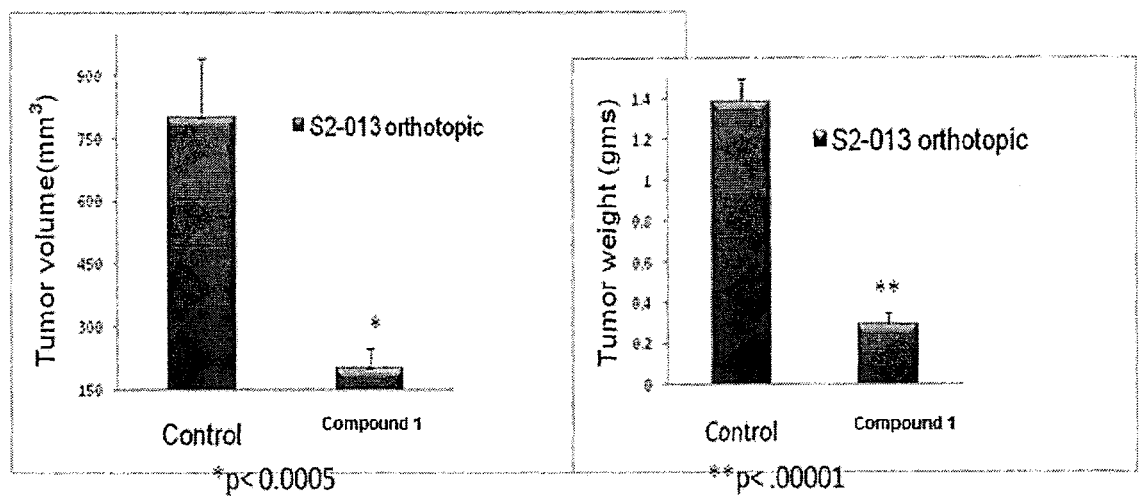

Figure 17. Tumor burden (volume or weight) analysis of Compound 1 treated or control mice.
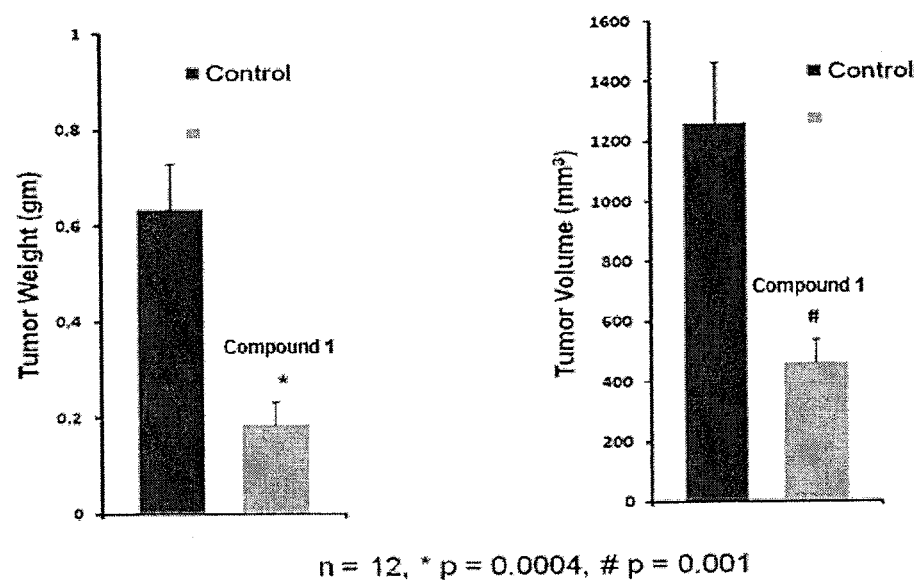

Figure 18. Tumor burden (volume or weight) analysis of Compound 1 treated or control mice.
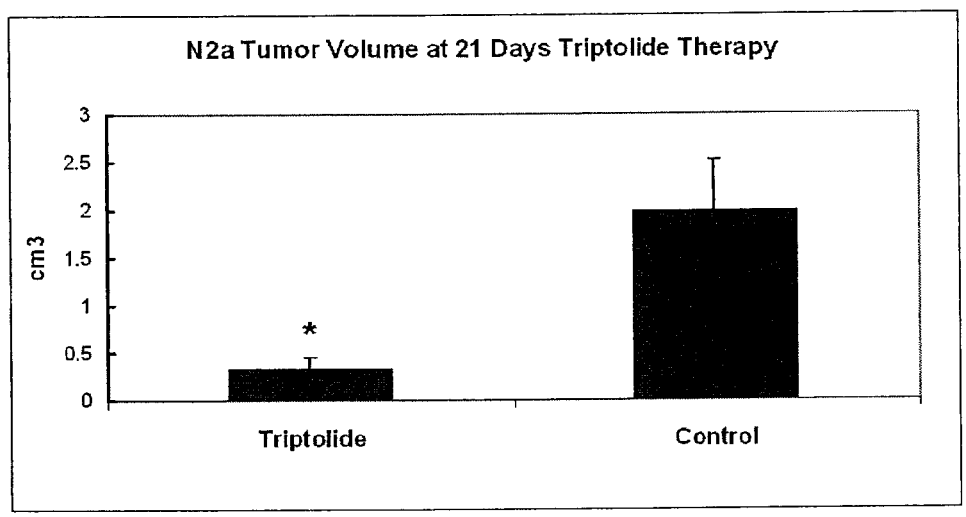
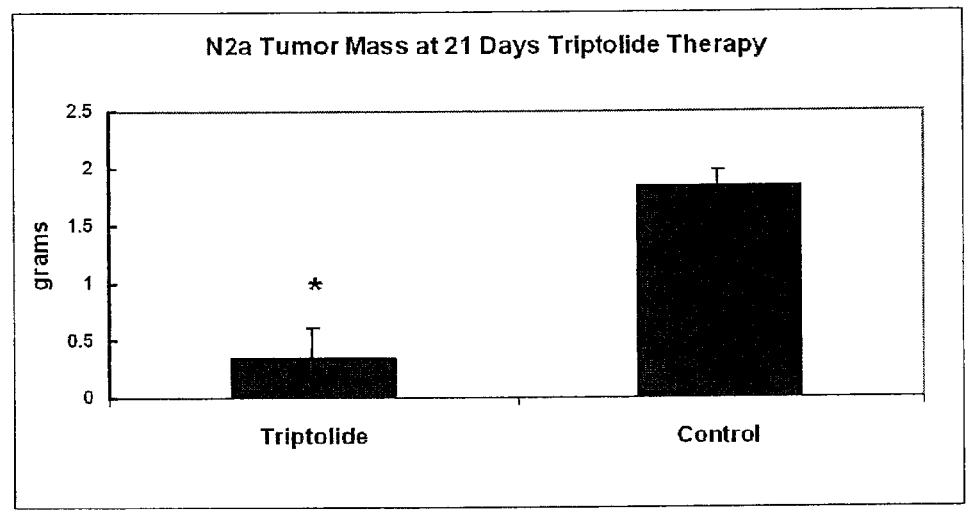
* P < 0.01 vs control
N = 3

Figure 19 illustrates cell viability (Neuroblastoma N2a and SKNSH) in the presence of triptolide.
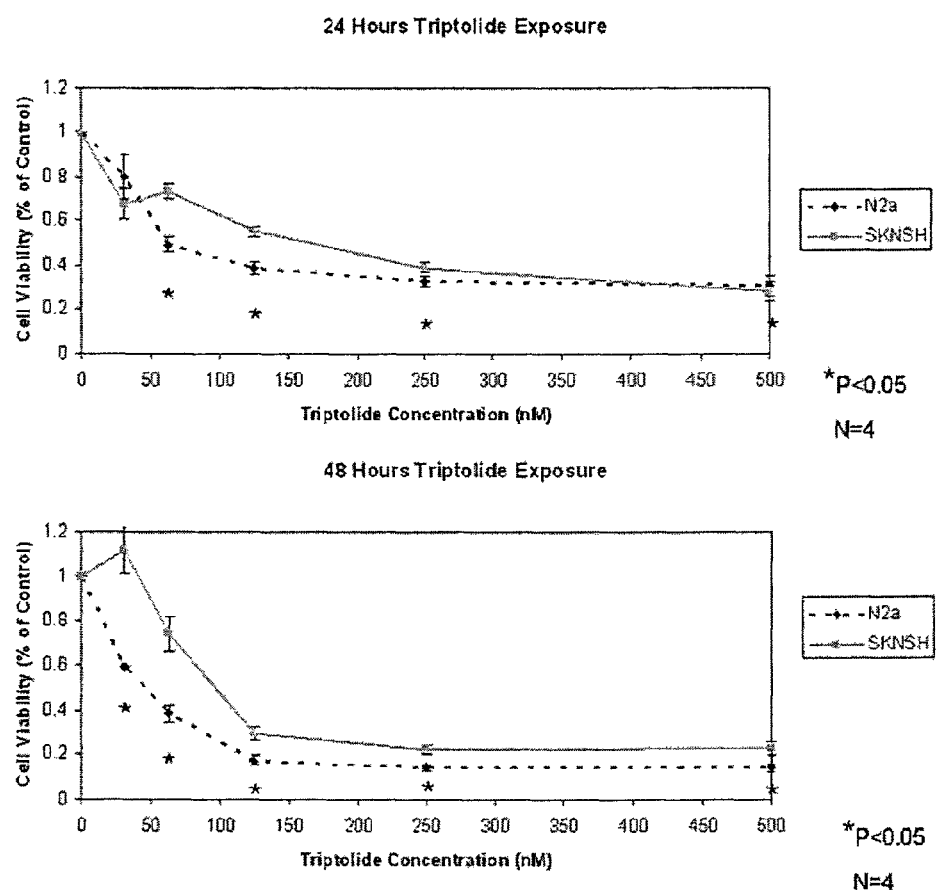

Figure 20 illustrates Caspase 3 activity in the presence of triptolide.
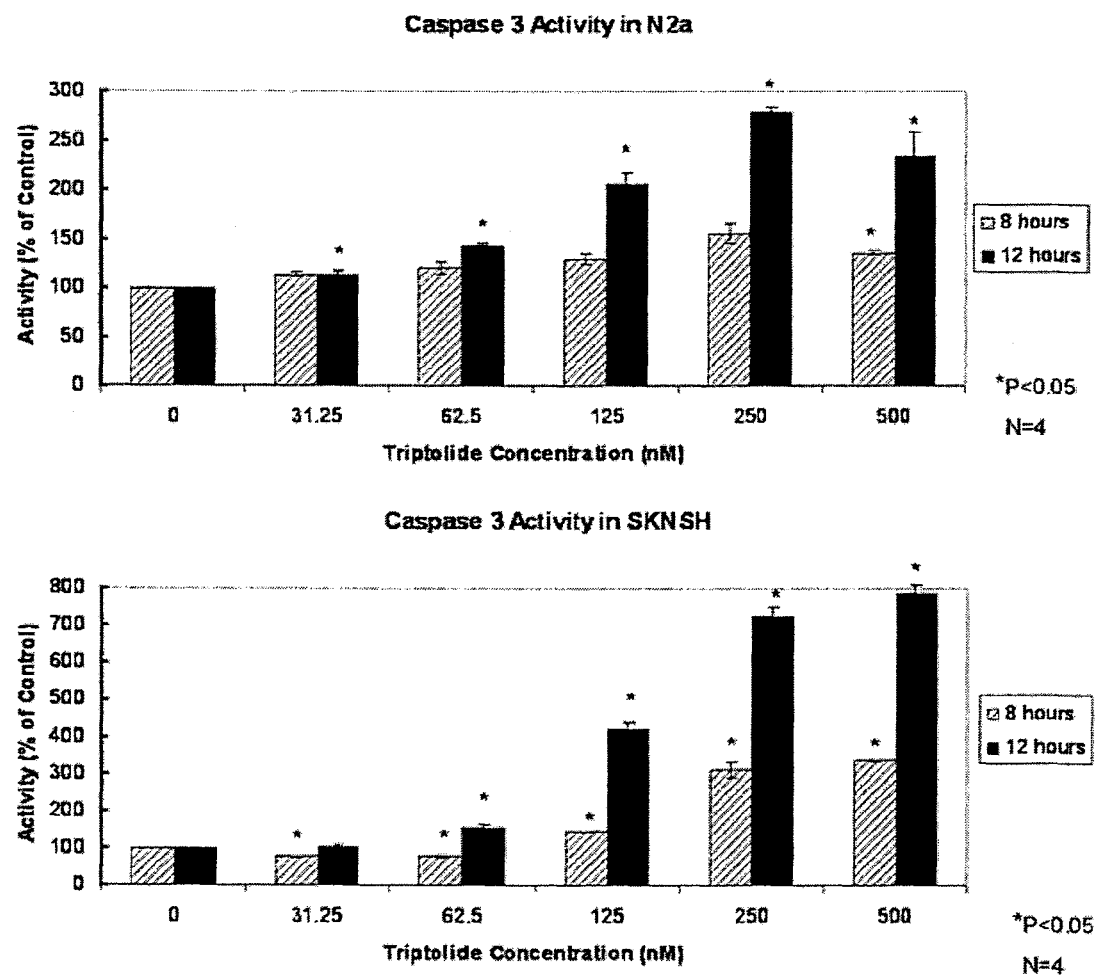

TRIPTOLIDE PRODRUGS

RELATED APPLICATIONS

This application is a division of U.S. patent application Ser. No. 13/319,316, which is a National Stage Application of International Application No. PCT/US2010/034117, filed on May 7, 2010, which claims priority to U.S. Provisional Application No. 61/176,249, filed on May 7, 2009. The contents of each of these applications are hereby incorporated herein by reference.

BACKGROUND OF THE INVENTION

Pancreatic cancer is a particularly aggressive and devastating disease with a five-year survival rate of less than 5%. No effective drug treatment is currently available which can effectively prolong patient survival. In 2006, over 35,000 new pancreatic cancer cases were reported with an almost equal number succumbing to the disease. Resistance to apoptosis has been investigated as a key factor in preventing response in patients to therapies to treat pancreatic and other cancers.

Triptolide is a naturally occurring compound obtained from the plant *Tripterygium wilfordii*. Triptolide is known to be useful in treating autoimmune diseases, transplantation rejection (immunosuppression), and possesses anticancer and anti-fertility effects as well as other biological effects (Qui and Kao, 2003, Drugs R.D. 4, 1-18). Triptolide has strong antitumor effects against xenograft tumors (for example, Yang et al. Mol. Cancer. Ther, 2003, 2, 65-72). Triptolide is an anti-apoptotic agent with multiple cellular targets that are implicated in cancer growth and metastasis. Triptolide inhibits NF-kB activation, induces bid cleavage, blocks induction of the survival gene p21 WAF1/$^{Cip1}$ (Wang et al. Journal of Molecular Medicine, 2006, 84, 405-415) and inhibits the function of heat shock transcription factor 1 (HSF1) thereby suppressing endogenous Hsp70 gene expression (Westerheide et al. 2006, Journal of Biological Chemistry, 281, 9616-9622). Triptolide also functions as a potent tumor angiogenesis inhibitor (He et al. 2010, Int. Journal of Cancer, 126, 266-278).

Several mechanisms exist in living cells that protect against adverse conditions, including cancer cells. The synthesis of a family of proteins referred to as heat-shock proteins (HSPs) is one such protective mechanism. Major HSPs include HSP90, HSP70, HSP60, HSP40 and smaller HSPs. HSPs can be present in most intracellular compartments, with HSP70 being primarily located in cytosol.

Dysregulated expression of HSP70 is known to be associated with many diseases including cancers. HSP70 is abundantly expressed in malignant tumors of various origins (For example: Hantschel et al. 2000, Cell Stress Chaperones, 5, 438-442), which render the tumor cells resistant to therapy and poor prognosis for the patient (Fuqua et al. 1994, Breast Cancer Res, Treatment 32, 67-71). Heat shock protein 70 (Hsp70) is known to be upregulated and over-expressed in pancreatic cancer cells as compared to normal cells. Furthermore, HSP70 has a protective effect on cancer cells inhibiting apoptosis of the cells. Inhibition of HSP70 in pancreatic cancer cells has been shown to increase apoptic cell death of these cells (See for example Aghdassi et al., Cancer Research, 67(2) p. 616-625 (2007)). Triptolide has been shown to inhibit pancreatic tumor growth and metastasis in mice. It was also shown that triptolide when used in combination with ionization radiation its therapeutic effect in pancreatic cancer treatment is enhanced (Wang et al. Proc. Amer. Assoc. Cancer Res. 2006, 47, abstract #4720 and Wang et al. Clin. Cancer Res. 2007, 13, 4891-4899). It is believed that the anticancer effect associated with triptolide occurs as a result of reducing levels of the protein HSP70 expressed in significant amounts by pancreatic cancer cells as compared to normal pancreatic cells. Thus, triptolide therapies have been of interest in the medical field for their potential treatment of cancers that over-express HSP70, including pancreatic cancer. See for example, Phillips et al., Cancer Research, 67(19), p. 9407-16 (2007).

There are, however, certain disadvantages associated with administering triptolide and different solutions to address these problems have been explored. One problem associated with native triptolide is that it is insoluble in aqueous solution. Another problem associated with natural triptolide is poor bioavailability and toxic side effects. Triptolide, triptolide derivatives and certain prodrugs having improved solubility and reduced toxicity are known. For example, Dai et al. U.S. Pat. No. 6,548,537 describes triptolide prodrugs having increased solubility and reduced toxicity.

The phosphonoxymethyl moiety per se is known in the art for purposes of forming prodrug compounds of certain pharmaceutical compounds. For example, Krise et al., J. Med. Chem., 42, pp. 3094-3100 (1999) describes preparation of N-phosphonooxymethyl prodrugs of certain compounds to improve water solubility.

Nevertheless, prodrugs must possess a number of properties in order to be practically useful. For instance, desirable prodrugs should be stable for formulation and administration. Additionally, once administered and present in the recipient's system, the prodrug must be successfully activated. Furthermore, both the prodrug and activated compound must be compatible with biological fluids, such as plasma and tissue homogenates. Ultimately, the activated compound initially delivered in prodrug form must have its desired therapeutic or pharmaceutical effect. These and other factors can be difficult to achieve simultaneously, or collectively balance, with certain types of compounds. Within the context of triptolide and triptolide prodrug compounds it has been difficult achieve improved aqueous solubility, effective bioavailability for oral dosage forms, faster in vivo release of triptolide, and relatively reduced or lower toxicity in combination with significant inhibition of cancer cell growth. For example, see Chassaing et al., Highly Water-Soluble Prodrugs of Anthelminthic Benzimidazole Carbamates: Synthesis, Pharmacodynamics and Pharmacokinetics, J. Med. Chem., 51(5), pp. 1111-1114 (2008).

Succinate prodrug forms of triptolide are known, but have been associated with certain disadvantages. See, for example, Harrousseau et al., Haematologica 2008, 93(s1), 14 Abstract 0038 and Kitzen et al. European Journal of Cancer 2009, 45, 1764-1772. Incomplete and variable conversion of the succinate prodrug of triptolide has been observed.

Thus, there exists a need in the medical and pharmaceutical fields for improved therapeutics for treating cancers including aggressive solid tumor cancers, such as pancreatic cancer. There also exists a further need for improved delivery or improved pharmacokinetic parameters or reduced toxicity of such therapeutics. There also exists a need for prodrug forms of triptolide that have improved solubility or that have faster release of the active compound triptolide or that have a more therapeutically effective release of the active compound triptolide or for prodrug forms of triptolide with improved bioavailability.

SUMMARY OF THE INVENTION

Accordingly, the invention provides a compound of the invention which is a compound of formula I:

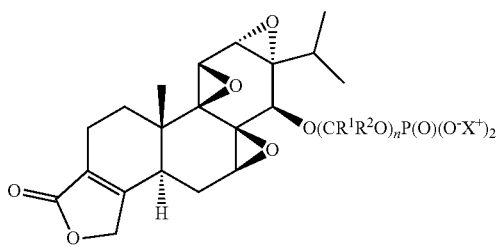

I wherein:
each $R^1$ is independently H, $(C_1-C_6)$alkyl, aryl$(C_1-C_6)$alkyl-, $(C_3-C_6)$cycloalkyl or aryl; and each $R^2$ is independently H, $(C_1-C_6)$alkyl, aryl$(C_1-C_6)$alkyl-, $(C_3-C_6)$cycloalkyl or aryl; or $R^1$ and $R^2$ together with the atom to which they are attached form a $(C_3-C_7)$cycloalkyl; wherein any alkyl or cycloalkyl of $R^1$ or $R^2$ may be optionally substituted with one or more (e.g. 1, 2, 3, 4 or 5) groups selected from halo, $(C_1-C_6)$alkoxy and $NR^aR^b$ and wherein any aryl of $R^1$ or $R^2$ may be optionally substituted with one or more (e.g. 1, 2, 3, 4 or 5) groups selected from halo, $(C_1-C_6)$alkyl, $(C_1-C_6)$alkoxy, $NR^aR^b$, nitro and cyano;

$R^a$ and $R^b$ are each independently selected from H, $(C_1-C_6)$alkyl, $(C_3-C_6)$cycloalkyl and aryl; or $R^a$ and $R^b$ together with the nitrogen to which they are attached form a pyrrolidino, piperidino, piperazino, azetidino, morpholino, or thiomorpholino;

n is 1, 2 or 3; and
each X is H;
or a salt thereof.

The invention also provides a pharmaceutical composition comprising a compound of formula I, or a pharmaceutically acceptable salt thereof, in combination with a pharmaceutically acceptable carrier.

The invention also provides a compound of formula I, or a pharmaceutically acceptable salt thereof for use in medical therapy.

The invention also provides a method for treating cancer (e.g. pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer or lymphoma tumors) in a mammal (e.g. a human), comprising administering a compound of formula I, or a pharmaceutically acceptable salt thereof, to the mammal (e.g. a human).

The invention also provides a compound of formula I, or a pharmaceutically acceptable salt thereof for use in the prophylactic or therapeutic treatment of cancer (e.g. pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer or lymphoma tumors.).

The invention also provides the use of a compound of formula I, or a pharmaceutically acceptable salt thereof for the manufacture of a medicament for the treatment of cancer (e.g. pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer or lymphoma tumors.) in a mammal (e.g. a human).

The invention also provides a method for inhibiting cancer cell growth in an HSP70-expressing cancer (e.g. pancreatic cancer, neuroblastoma, breast cancer, colon cancer, gastric cancer, liver cancer or glioblastoma) in a mammal (e.g. a human) comprising administering an inhibitory effective amount of a compound of formula I, or a pharmaceutically acceptable salt thereof, to the mammal (e.g. a human).

The invention also provides a compound of formula I, or a pharmaceutically acceptable salt thereof for use in the prophylactic or therapeutic inhibition of cancer cell growth in an HSP70-expressing cancer (e.g. pancreatic cancer, neuroblastoma, breast cancer, colon cancer, gastric cancer, liver cancer or glioblastoma).

The invention also provides the use of a compound of formula I, or a pharmaceutically acceptable salt thereof for the manufacture of a medicament for the inhibition of cancer cell growth in an HSP70-expressing cancer (e.g. pancreatic cancer, neuroblastoma, breast cancer, colon cancer, gastric cancer, liver cancer or glioblastoma) in a mammal (e.g. a human).

The invention also provides novel processes and novel intermediates disclosed herein that are useful for preparing compounds of formula I or salts thereof, for example, those described in Schemes 1-2.

BRIEF DESCRIPTION OF THE FIGURES

FIG. 13 illustrates survival analysis of the compound 1 treated mice and control mice.

FIG. 14 illustrates survival analysis of the compound 1 treated mice and control mice.

FIG. 15 illustrates tumor burden (volume and weight) for the compound 1 triptolide and vehicle treated mice.

FIG. 16 illustrates tumor burden (volume and weight) for compound 1 and vehicle treated mice.

FIG. 17 illustrates tumor burden (volume and weight) for compound 1 and vehicle treated mice.

FIG. 18 illustrates tumor volume for compound and vehicle treated mice.

FIG. 19 illustrates cell viability (Neuroblastoma N2a and SKNSH) in the presence of triptolide.

FIG. 20 illustrates Caspase 3 activity in the presence of triptolide.

DETAILED DESCRIPTION OF THE INVENTION

Definitions

Figure 1:
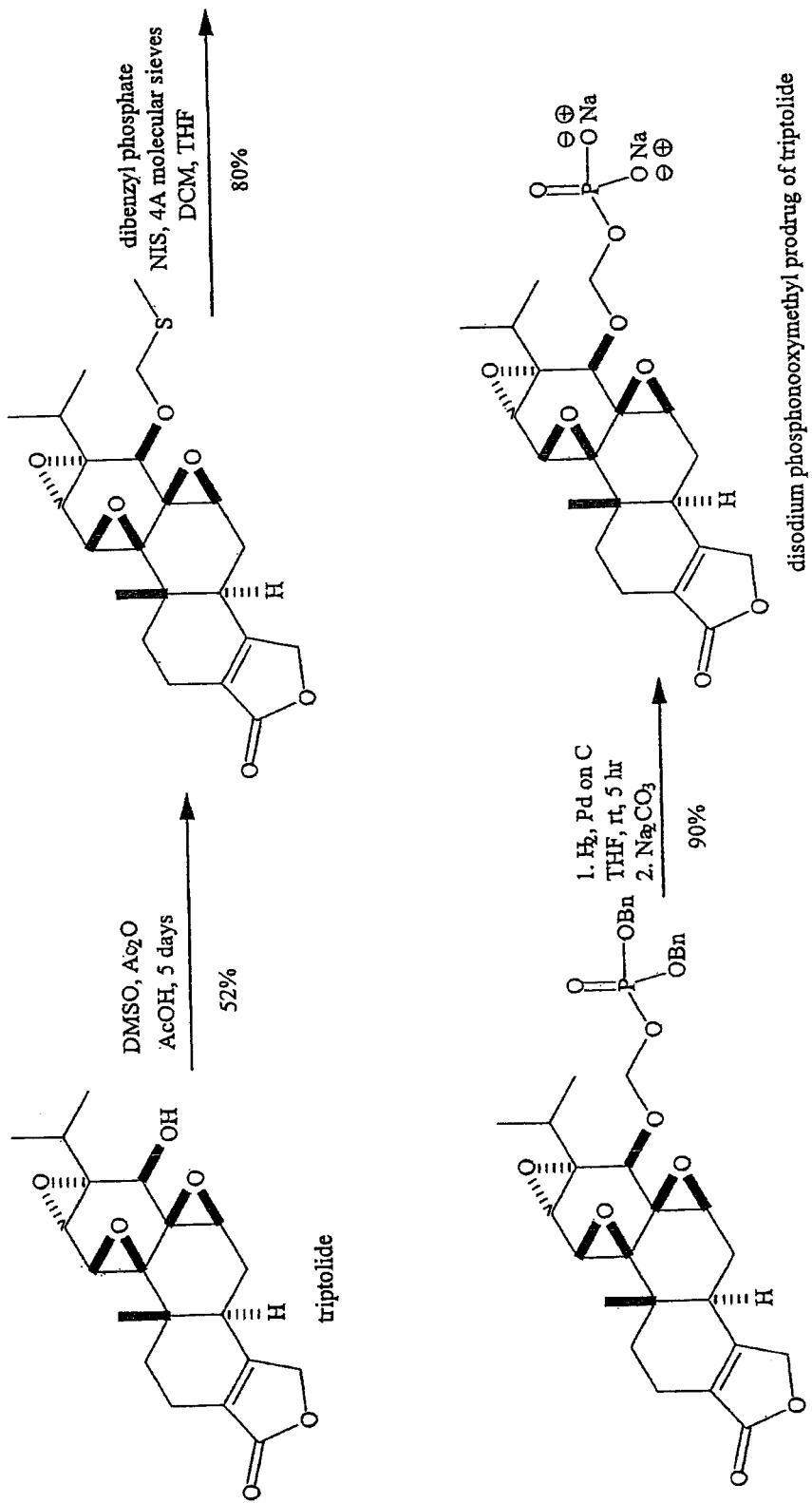
FIG. 1 illustrates a chemical reaction diagram for preparing the compound 1.

The term "$(C_1-C_6)$alkyl" as used herein refers to alkyl groups having from 1 to 6 carbon atoms which are straight or branched groups. This term is exemplified by groups such as methyl, ethyl, n-propyl, iso-propyl, n-butyl, t-butyl, isobutyl, n-pentyl, neopentyl, and n-hexyl, and the like.

The term "$(C_1-C_6)$alkoxy" as used herein refers to the group $(C_1-C_6)$alkylO— wherein $(C_1-C_6)$alkyl is as defined herein. This term is exemplified by groups such as methoxy, ethoxy, propoxy, isopropoxy, butoxy, iso-butoxy, sec-butoxy, pentoxy, 3-pentoxy, or hexyloxy, and the like.

The term "$(C_3-C_7)$cycloalkyl" as used herein refers to a saturated or partially unsaturated cyclic hydrocarbon ring system comprising 3 to 7 carbon atoms. This term is exemplified by such groups as cyclopropyl, cyclobutyl, cyclopentyl, cyclohexyl, cyclohexene, or cycloheptane, and the like.

The term "aryl" as used herein refers to a phenyl radical or an ortho-fused bicyclic carbocyclic radical having about nine to ten carbon ring atoms in which at least one ring is aromatic. This term is exemplified by such groups phenyl, indanyl, indenyl, naphthyl, 1,2-dihydronaphthyl and 1,2,3,4-tetrahydronaphthyl.

The term "aryl($C_1-C_6$)alkyl-" as used herein refers to the group aryl-($C_1-C_6$)alkyl- wherein ($C_1-C_6$)alkyl and aryl are as defined herein. This term is exemplified by such groups as benzyl and phenethyl and the like.

As used herein, the term "comprising" means the elements recited, or their equivalent in structure or function, plus any other element(s) which are not recited. The terms "having" and "including" are also to be construed as open ended unless the context suggests otherwise. Terms such as "about," "generally," "substantially," and the like are to be construed as modifying a term or value such that it is not an absolute, but does not read on the prior art. Such terms will be defined by the circumstances and the terms that they modify are understood by those of skill in the art. This includes at the very least the degree of expected experimental error, technique error, and instrument error for a given technique used to measure a value.

The phrases "therapeutically effective amount" and "pharmaceutically effective amount" are used herein, for example, to mean an amount sufficient to reduce or inhibit in vivo cancerous cell growth upon administration to a living mammal. The phrases are meant to refer to the amount determined to be required to produce the physiological effect intended and associated with the given active ingredient, as measured according to established pharmacokinetic methods and techniques, for the given administration route.

The phrase "inhibitory effective amount" as used in association with the amount of active compound and composition of the invention is meant to refer, for example, to exhibited antitumor properties as demonstrated using standard cell culture assay techniques.

As used herein, the term "prodrug" is meant to refer to a pharmaceutical compound that requires further metabolism (including but not limited to the liver) before becoming biologically active.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms, for example, by resolution of the racemic form by recrystallization techniques, by synthesis from optically-active starting materials, by chiral synthesis, or by chromatographic separation using a chiral stationary phase.

A salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts and inorganic salts.

The term "organic cation or inorganic cation" or "cationic organic or inorganic salt" include organic cations or inorganic cations (e.g. metal or amine salts) that are well known in the art and include cationic moieties that can form an ionic association with the O moieties on the compound and not significantly adversely affecting the desired properties of the prodrug for purposes of the invention. The term "pharmaceutically acceptable organic cations or inorganic cations" or "pharmaceutically acceptable cationic organic or inorganic salt" include the "organic cations or inorganic cations" which are pharmaceutically acceptable for use in a mammal and are well known in the art.

Organic cations or inorganic cations include but are not limited to lithium, sodium, potassium, magnesium, calcium, barium, zinc, aluminium and amine cations. Amine cations include but are not limited to cations derived from ammonia, triethylamine, tromethamine (TRIS), triethanolamine, ethylenediamine, glucamine, N-methylglucamine, glycine, lysine, ornithine, arginine, ethanolamine, choline and the like. In one embodiment, the amine cations are cations wherein $X^+$ is of the formula $YH^+$ wherein Y is ammonia, triethylamine, tromethamine (TRIS), triethanolamine, ethylenediamine, glucamine, N-methylglucamine, glycine, lysine, ornithine, arginine, ethanolamine, choline and the like.

In one embodiment suitable cationic organic or inorganic salts that can be used include cationic moieties that can form an ionic association with the O moieties on the compound and not significantly adversely affecting the desired properties of the prodrug for purposes of the invention, e.g., increased solubility, stability, and rapid hydrolytic release of the active compound form. Preferably, X is selected from Li⁺, K⁺, or Na⁺. More preferably, X is Na⁺ thus forming the disodium salt.

Pharmaceutically acceptable salts can also include salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts. Salts, including pharmaceutically acceptable salts may be obtained using standard procedures well known in the art, for example by reacting a sufficiently basic compound such as an amine with a suitable acid affording a physiologically acceptable anion.

The invention includes both the free acid (e.g. —OP(O)(OH)₂), mono-salts (e.g. —OP(O)(OH)(O⁻ X⁺)) and di-salts (e.g. —OP(O)O⁻ X⁺)₂) of the compounds of formula I. The acid and the salts may be purified by a variety of techniques well known in the art such as chromatography, followed by lyophilization or recrystallization.

It will be appreciated by those skilled in the art that a compound of formula I wherein X⁺ is an organic cation or inorganic cation can be converted to a compound of formula I comprising one or more different organic or inorganic cations. Such a conversion can be accomplished using a variety of well known techniques and materials including but not limited to ion exchange resins, ion exchange chromatography and selective crystallization.

A specific value for $R^1$ is H or $(C_1-C_6)$alkyl.
Another specific value for $R^1$ is H.
Another specific value for $R^1$ is $(C_1-C_6)$alkyl.
Another specific value for $R^1$ is methyl or ethyl.
A specific value for $R^2$ is H or $(C_1-C_6)$alkyl.
Another specific value $R^2$ is H.
A specific value for X⁺ is H.
Another specific value X⁺ is lithium, sodium, potassium, magnesium, calcium, barium, zinc or aluminium.
Another specific group of compounds of formula I are compounds wherein X⁺ is of the formula HY⁺ wherein Y is ammonia, triethylamine, tromethamine, triethanolamine, ethylenediamine, glucamine, N-methylglucamine, glycine, lysine, ornithine, arginine, ethanolamine or choline.
Another specific value for X⁺ is Li⁺, K⁺ or Na⁺.
Another specific value for X⁺ is Na⁺.
A specific compound of formula I is 4-O-phosphonooxymethyltriptolide disodium salt, 14-O-phosphonooxyethyltriptolide disodium salt or 14-O-phosphonooxypropyltriptolide disodium salt, or a salt thereof.

A specific group of compounds of formula I are compounds formula Ia:

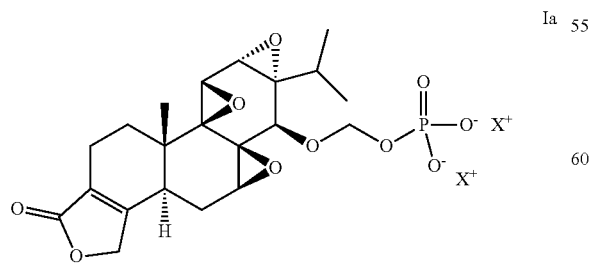

Ia wherein X⁺ is a pharmaceutically acceptable organic cation or inorganic cation.

Another specific group of compounds of formula I are compounds formula Ia:

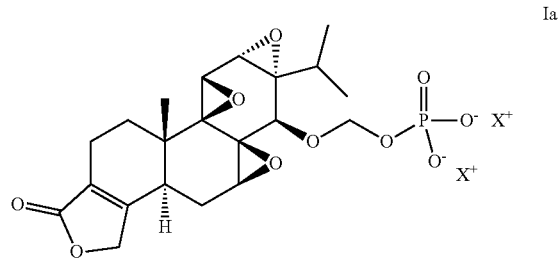

Ia wherein X⁺ is a pharmaceutically acceptable cationic organic or inorganic salt.

Processes which can be used to prepare compounds of formula I and intermediates useful for preparing compounds of formula 1 are shown in Scheme 1 and Scheme 2.

Scheme 1

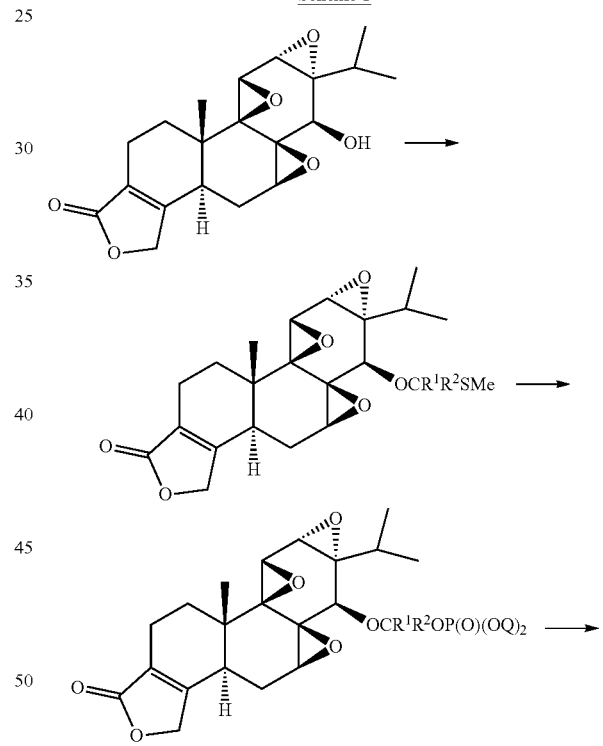

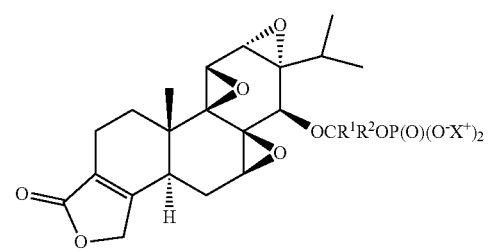

wherein Q is a protecting group such as benzyl or tertbutyl.

Scheme 2

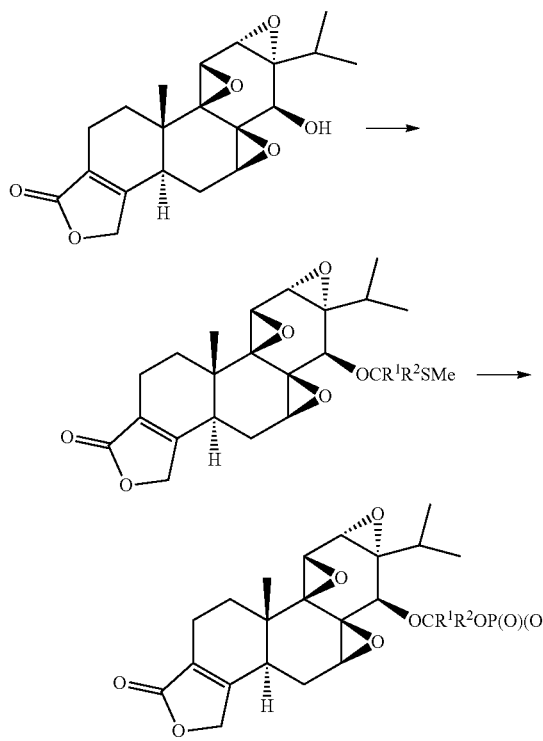

A compound of formula I can be prepared by removing one or more protecting groups from a compound of formula IA:

IA

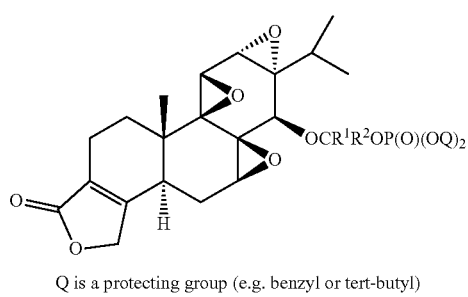

Q is a protecting group (e.g. benzyl or tert-butyl)

to provide the corresponding compound of formula I. Thus, the intermediate of formula IA is useful for preparing a compound of formula I.

A compound of formula I can also prepared by converting the —SMe group from a compound of formula IB:

IB

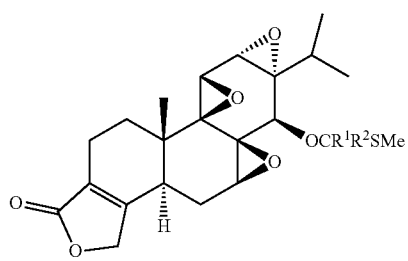

to a —OP(O)(O⁻X⁺)$_2$ group to provide the corresponding compound of formula I. Thus, the intermediate of formula IB is useful for preparing a compound of formula I.

A compound of formula I can also be prepared by removing one or more protecting groups from a compound of formula IC:

IC

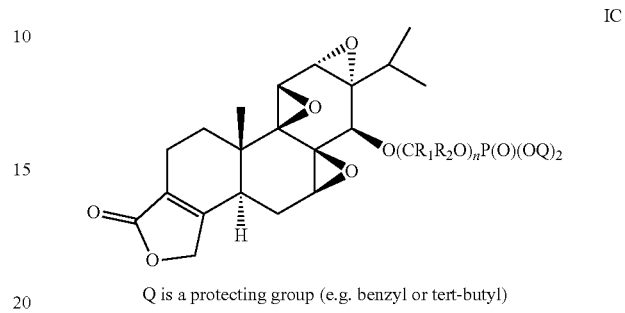

Q is a protecting group (e.g. benzyl or tert-butyl)

to provide the corresponding compound of formula I. Thus, the intermediate of formula IC is useful for preparing a compound of formula I.

A compound of formula I can also prepared by converting the —SMe group from a compound of formula ID:

ID

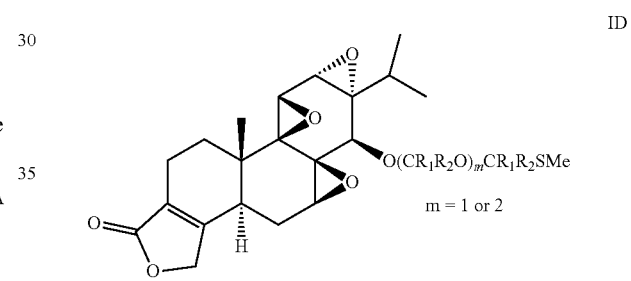

m = 1 or 2 to a —OP(O)(O⁻ X⁺)$_2$ group to provide the corresponding compound of formula I. Thus, the intermediate of formula ID is useful for preparing a compound of formula I.

Accordingly, the invention provides a method:

a) for preparing a compound of formula I comprising deprotecting a corresponding compound of formula IA bearing one or more protecting groups to provide the compound of formula I.

b) for preparing a compound of formula I comprising converting the —SMe group from a compound of formula IB to a —OP(O)(O⁻ X⁺)$_2$ group to provide the compound of formula I.

c) for preparing a compound of formula I comprising deprotecting a corresponding compound of formula IC bearing one or more protecting groups to provide the compound of formula I.

d) for preparing a compound of formula I comprising converting the —SMe group from a compound of formula ID to a —OP(O)(O⁻ X⁺)$_2$ group to provide the compound of formula I.

e) for preparing a salt of a compound of formula I comprising treating a corresponding compound of formula I with an acid (e.g. an organic acid or inorganic acid) or base (e.g. an alkali base or alkaline base) to provide the salt of the compound of formula I.

f) for converting the a compound of formula I wherein one or more X⁺ is a cationic organic or inorganic salt to a compound of formula I wherein one or more X⁺ is a different cationic organic or inorganic salt.

The compound of the invention can be formulated into pharmaceutical compositions as well by combining together with a pharmaceutically acceptable carrier. Pharmaceutical compositions can be prepared in accordance with well-known compounds and techniques readily available to those skilled in the pharmaceutical field. For purposes of the invention, the pharmaceutically acceptable carrier can be any conventional and readily available biologically compatible or inert substance which is chemically compatible with the active pharmaceutical ingredient and does not significantly attenuate its intended therapeutic effect upon formulation or delivery. Pharmaceutically acceptable salts can be prepared using standard procedures and techniques well known in the art.

The solid form of a compound of the invention can be a nanoparticle and thus formulated as a nanoparticle. Accordingly, the invention provides for nanoparticles of a compound of formula I and compositions that comprise nanoparticles of a compound of formula I.

The triptolide prodrug compounds of the invention can be formulated using a variety of excipient formulations and prepared in various dosage forms as described below. The chemical properties and attributes associated with the compounds of invention also can afford the preparation of an oral solid dosage forms of the compounds of the invention.

The compound of the invention can be formulated as pharmaceutical compositions and administered to a recipient in a variety of forms suitable for the desired particular administration route or system. Administration routes can include but are limited to oral routes, parenteral routes, intravenous routes (including intravenous routes by pump injection), intramuscular routes, topical routes including eye drops, subcutaneous routes and mucosal routes. Compounds of the invention can be administered systemically, e.g. orally, in combination with a pharmaceutically acceptable carrier such as an inert diluent or assimilable edible carrier. Thus the pharmaceutical composition comprising the compounds of the invention as the active ingredient can be prepared in a variety of dosage forms. For example, the compositions can be encapsulated in hard or soft capsules (e.g., gelatin or vegetable-derived capsular materials). The compositions can be compressed into ingestible or transmucosal tablet form, troches, capsules, elixirs, suspensions, syrups, wafers, suppositories and the like. The amount of active ingredient can vary according to the specific desired pharmaceutically effective dosage amount.

Tablets, troches, pills, capsules, and the like can contain additional ingredients such as binders (such as gum tragacanth, acacia, corn starch or gelatin); excipients such as dicalcium phosphate; disintegrants such as corn starch, potato starch, alginic acid, and the like; lubricants (such as magnesium stearate) which can be used for tablet compression techniques, for example; sweeteners such as sucrose, fructose, lactose or aspartame; and flavoring agents such as peppermint, wintergreen, cherry, and the like. Additional ingredients which may be included in compositions of the invention are mannitol, urea, dextranes, and lactose non-reducing sugars.

When the dosage form is a capsule, it can contain a liquid carrier including polyethylene glycol, vegetable oil, etc. Other materials that can be used with certain dosage forms include gelatin, wax, shellac, sugar, and the like. Syrups or elixir forms can contain sucrose, fructose as sweeteners, methyl and propylparabens as preservatives, dyes and colorants, and flavoring agents.

When administered intravenously or intraperitoneally by infusion or injection, solutions of the active ingredient and its salts can be prepared in, for example, water or saline optionally containing a non-toxic surfactant. Dispersions can be prepared in glycerol, liquid polyethylene glycols, triacetin, and mixtures thereof and in oils. Storage conditions may necessitate the inclusion of a preservative as well.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Accordingly, the invention includes sterile preparation of a compound of the invention. The invention also includes non-sterile preparations of a compound of the invention.

Injectible or infusible pharmaceutical dosage forms can include sterile aqueous solutions or dispersions or sterile powders comprising the active compounds of the invention prepared for extemporaneous formulation. Liquid carriers can include solvents or liquid dispersion mediums comprising water, ethanol, a polyol (e.g., glycerol, propylene glycol, polyethylene glycols), and the like. Various agents can be added to inhibit or prevent antimicrobial activity, such as parabens, chlorobutanol, phenol, sorbic acid, thimerosal, and the like.

Compounds and compositions of the invention can be administered as a single dose or in multiple dose intervals. The dosage amount, dosage form, route of administration, and the particular formulation ingredients can vary corresponding to the desired plasma concentration and pharmacokinetics involved. A significant aspect of the invention is that the particular compounds of the invention may afford an improved and effective oral dosage form administration route by virtue of the characteristics and properties associated with the inventive compound structure and substituent location.

For topical administration, it will generally be desirable to administer the compounds of the invention to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula Ito the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 3 to about 100 µg/kg of body weight per day (e.g. from about 6 to about 96 µg/kg of body weight per day or from about 6 to about 48 µg/kg of body weight per day, or from about 6 to about 24 µg/kg of body weight per day, or from about 12 to about 24 µg/kg of body weight per day).

The compound is conveniently formulated in unit dosage form; for example, containing from about 80 µg to about 8000 µg, conveniently from about 480 µg to about 7680 µg, conveniently from about 480 mg to about 3840 µg, and conveniently from about 960 µg to about 1920 µg. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of cancer (e.g. pancreatic cancer, ovarian cancer, colorectal cancer, non-Hodgkin lymphoma, leukemia, acute and chronic myelogenous leukemia, neuroblastoma, thyroid carcinoma, osteosarcoma, breast, prostate cancer, esophageal cancer, bladder cancer, gastric carcinoma, urothelial cancer, glioblastoma multiforme, colon cancer, uterine cervical cancer, fibrosarcoma, squamous cell carcinoma, multiple myeloma, cholangiocarcinoma, non-small cell lung cancer) as a radiation sensitizer for cancer cells, inflammatory diseases, rheumatic diseases, auto-immune diseases, polycystic kidney disease, nephritis., transplantation graft survival (kidney, heart), pulmonary hypotension, lung inflammation, lung fibrosis, neuroprotection, cerebral ischemia/reperfusion injury, Parkinsonism and corneal ulcers. Examples of such agents include 5-fluorouracil, TRAIL (TNF-related apoptosis-inducing ligand), DR-4/5 activating antibodies, cyclophosphamide, hydroxydaunorubicin (doxorubicin), oncovin (vincristine), paclitaxel, doxetaxel, cisplatin, carboplatin, CPT-11, bortezimib and prednisone-prednisolone. Accordingly, in one embodiment the invention also provides a composition comprising a compound of formula I, or a pharmaceutically acceptable salt thereof, at least one other therapeutic agent, and a pharmaceutically acceptable diluent or carrier. The invention also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to an animal (e.g. mammal) to treat cancer (e.g. pancreatic cancer, ovarian cancer, colorectal cancer, non-Hodgkin lymphoma, leukemia, acute and chronic myelogenous leukemia, neuroblastoma, thyroid carcinoma, osteosarcoma, breast, prostate cancer, esophageal cancer, bladder cancer, gastric carcinoma, urothelial cancer, glioblastoma multiforme, colon cancer, uterine cervical cancer, fibrosarcoma, squamous cell carcinoma, multiple myeloma, cholangiocarcinoma, non-small cell lung cancer), an inflammatory disease, a rheumatic disease, an auto-immune disease, a polycystic kidney disease, nephritis, transplantation graft survival (kidney, heart), pulmonary hypotension, lung inflammation, lung fibrosis, neuroprotection, cerebral ischemia/reperfusion injury, Parkinsonism, corneal ulcers or colitis. In another embodiment the invention also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to an animal (e.g. mammal) to sensitize cancer cells, coat stents (drug elution), repair spinal cord repair, or for use as in male and female contraception in animals. The following documents relate to triptolide in combination with other therapeutic agents (1. Chen, Y. W. et al., Anticancer Drugs, 2010, 21(5), 502-13. 2. Xu B. et al., Cancer Lett., 2010, 291(2), 200-208. 3. Borja-Cacho, D. et al., J. Gastrointest. Surg., 2010, 14(2), 252-60. Westfall S. D. et al., Chemotherapy, 2008, 54(1), 67-76. 4. Tang X. Y. et al., Postgrad. Med. J., 2007, 83(979), 338-43. 5. Panichakul T. et al., Anticancer Res. 2006, 26(1A), 259-65. 6. Pediatr. Blood Cancer, 2008, 51(6):754-97. Matsui et al. Oncogene, 2008, 27, 4603-4614. 7. Chang et al., The Journal of Biological Chemistry, 2001 276, 2221-2227. 8. Westfall et al., Chemotherapy, 2008, 54(1), 67-76. 9. Carter et al., Blood, 2008, Vol. 111, No. 7, pp. 3742-3750. 10. Borja-Cacho et al., J. Gastrointest Surg., 2010, 14, 252-260. 11. Tang et al., Postgraduate Medical Journal 2007, 83, 338-343. 12. Cen et al., Anti-Cancer Drugs, 2010, 21(5), 502-513. 13. Kapoor, Int. J. Mol. Med. 2008, 22(4), 489-96. 14. Fidler et al., Molecular Cancer Therapeutics, 2003, 2, 855).

An important aspect of the invention is that compounds of the invention afford desirable combinations of pharmacokinetic properties, physical properties and therapeutic advantages as compared to other triptolide prodrug forms. The triptolide prodrug compounds of the invention exhibit desirable combination of attributes including chemical stability, enhanced solubility, and rapid metabolic release of the active triptolide from the prodrug form. Collectively, these properties provide improved therapeutic anticancer effects. Such effects include the effective inhibition of pancreatic cancer cells by inhibiting the protective effects afforded by HSP70 within cells and resistance to apoptosis and treatments.

Figure 2:
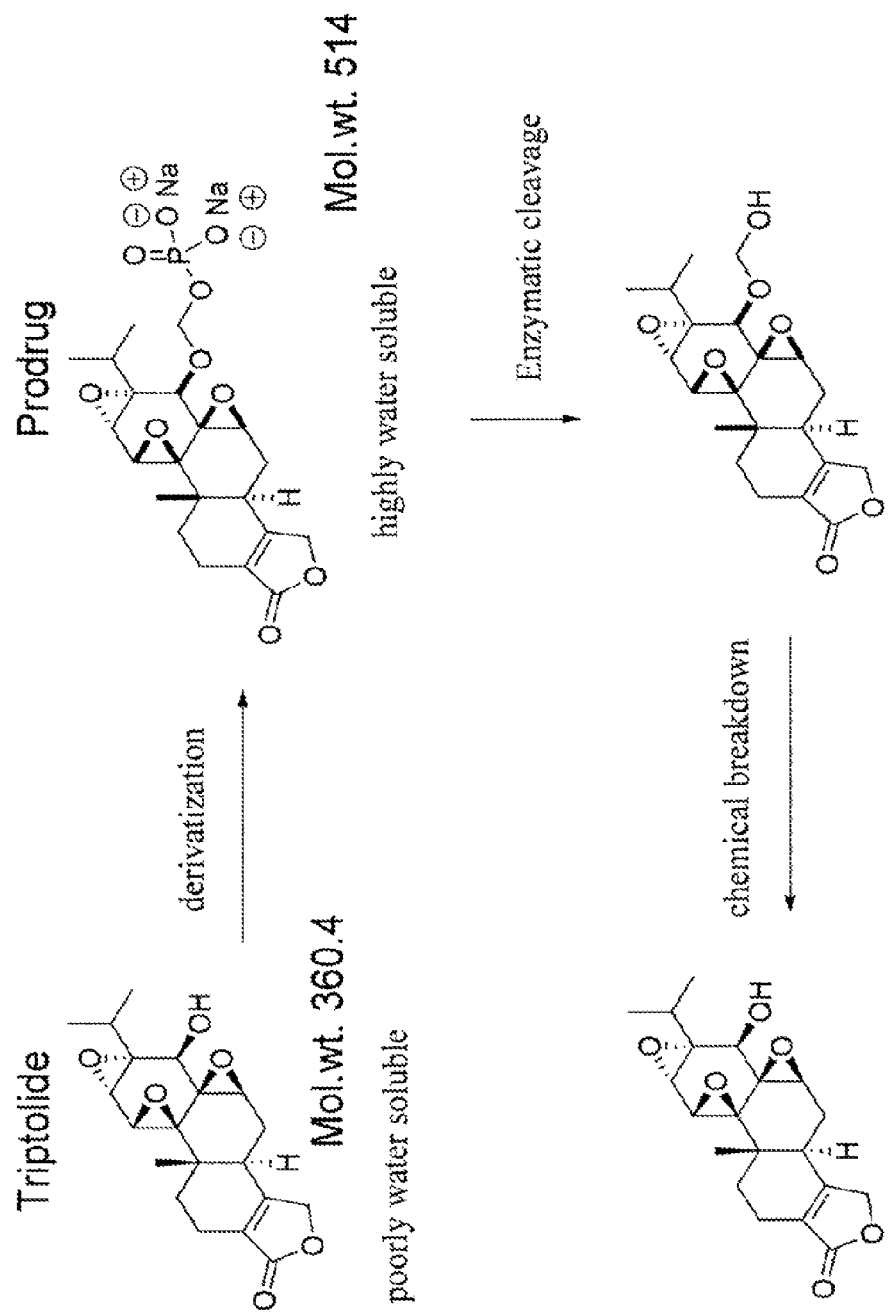
FIG. 2 illustrates a chemical reaction diagram showing triptolide being derivatized to compound 1 and the subsequent enzymatic cleavage—chemical breakdown of compound 1 to release triptolide.

The chemical pathway of the metabolic and enzymatic cleavage of the triptolide prodrug of Example 1 is shown in FIG. 2. The starting native compound (non-prodrug form) triptolide has poor water solubility characteristics. The prepared compound of Example 1 exhibits a high level of solubility. When subjected to enzymatic cleavage and metabolism, the compound of Example 1 ultimately releases the active form of the triptolide compound.

The compounds and compositions of the invention can be employed as a method for treating solid tumor cancers in a mammal in need of such treatment comprising administering a pharmaceutically effective amount of a compound as described above as the active ingredient. As used in the context of methods of treatment, the term "mammal" includes humans.

The compound and composition of the invention can be effective to inhibit in vitro and in vivo cancer cell growth of HSP70-expressing cancers. Examples of HSP70-expressing cancers include pancreatic cancer, breast cancer, lung cancer, neuronal cancer, leukemia, neuroblastoma, colon cancer, gastric cancer, liver cancer, and glioblastoma.

Accordingly, in one embodiment, the invention includes the inhibition of a cancer cell population of cells exhibiting over-expression of heat-shock protein HSP70 by the administration of a compound of formula I. Of specific importance to the invention is the effective cell inhibition effect upon HSP70-expressing pancreatic cancer cells, such as Mia-Paca, Panc-1 and S2VP10 cells. Accordingly, in another embodiment the invention provides a method for treating an S2 cancer (e.g. an S2VP10 or 52013 cancer) in a mammal (e.g. a human). comprising administering a compound of formula I, or a pharmaceutically acceptable salt thereof, to a mammal (e.g. a human).

In both in vitro and living mammalian systems, the enzyme alkaline phosphatase converts the compound of Example 1 into the active triptolide form as demonstrated in the examples herein. The enzymatic hydrolysis half life (t½) for the compound of Example 1 indicates a relatively rapid conversion rate and, consequently, faster release of the active therapeutic form of the compound.

Triptolide is used to treat a variety of diseases such as inflammatory diseases. Triptolide has also been implicated as a therapeutic agent to treat a variety of diseases. These diseases include cancer (e.g. pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer, lymphoma tumors), autoimmune diseases, transplant rejection, polycystic kidney disease, inflammatory diseases, asthma, rheumatoid arthritis, systemic lupus erythematosus and nephritis. Triptolide has also been discussed in the coating of stents (drug elution), spinal cord repair, colitis, and contraception in male and female animals. Accordingly, the invention includes but is not limited to the use of the compounds of formula I to treat diseases including cancer (e.g. pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer, lymphoma tumors), autoimmune diseases, transplant rejection, polycystic kidney disease, inflammatory diseases, asthma, rheumatoid arthritis, systemic lupus erythematosus and nephritis. Compounds of formula I can also be can also be used for coating stents (drug elution), spinal cord repair, colitis, and contraception in male and female mammals.

The following documents are directed to triptolide and cancer (1. AML: Carter et al., Blood, 2008, 111(7), 3742-3750. 2. Anaplastic thyroid carcinoma: Mol. Pharmacol., 2009, 75(4), 812-9. 3. Bladder cancer: Yang et al., Mol. Cancer. Ther., 2003, 2(1), 65-72. 4. B16 Melanoma: Yang et al., Mol. Cancer. Ther. 2003, 2(1), 65-72. 5. Breast Cancer: Liang et al., Cancer Letters, 270(2), 2008, 337-341. Liu et al., Phytomedicine, 2009, 16(11), 1006-1013. 6. Cervical Cancer Wang et al., J. Mol. Med., 2006, 84(5), 405-15. 7. Cholangiocarcinoma: Tengchaisri et al., Cancer Letters, 1998, 133(2), 169-175. 8. CML: Lou et al., Leukemia and Lymphoma, 2004, 45, 373-376. 9. Colon: Tang et al., Postgraduate Medical Journal 2007, 83, 338-343. 10. Esophageal cancer: Boult et al., B. J. Cancer, 2008, 89, 1985-92. 11. Fibrosarcoma: Kiviharju et al., Clinical Cancer Research, 2002, 8, 2666-2674. 12. Miyata et al., Biochem. Biophys. Res. Commun., 2005, 336(4), 1081-6. 13. Gastric Cancer: Jiang., Oncogene, 2001, 20(55), 8009-18. 14. Yang et al., Mol. Cancer. Ther. 2003, 2(1), 65-72. 15. Glioblastoma Multiforme Lin et al., J. Int. Med. Res., 2007, 35(4), 490-6. 16. Kapoor, Int. J. Mol. Med., 2008, 22(4), 489-96. 17. Human Prostatic Epithelial Cells: Kiviharju et al., 2002., Clinical Cancer Research, 8, 2666-2674. 18. Leukemias including AML: Carter et al., Blood, 2006, 108(2), 630-7. 19. Multiple myeloma: Yinjun et al., Leuk. Res. 2005 29(1), 99-105. 20. Neuroblastoma: Antonoff et al., Surgery, 2009, 146(2), 282-90.

21. non-Hodgkin lymphoma: Zhang et al., Acta Pharmacologica Sinica, 2006, 27, 1438-1446. 22. Non-small cell lung cancer: Chang et al., The Journal of Biological Chemistry, 276, 2221-2227. 23. Osteosarcoma: Wang et al., Pediatr. Blood Cancer. 2008, 51(6), 754-9. 24. Ovarian Cancer: Westfall et al., Chemotherapy, 2008, 54(1), 67-76. 25. Pancreatic Cancer: Wang et al., J. Mol. Med. 2006, 84(5), 405-15., Zhou et al., World J., Gastroenterol, 2008, 14(10), 1504-1509., Wang et al. Clincal Cancer Research 2007, 13, 4891., Phillips, Saluja et al., Cancer Res., 2007.

Squamous cell carcinoma; Miyata et al., Biochem. Biophys. Res. Commun., 2005, 336(4), 1081-6. 26. Thyroid carcinoma: Zhu et al., Oncol Rep., 2009, 22(6), 1397-401. 27. Uterine cervical carcinoma: Miyata et al., Biochem. Biophys. Res. Commun., 2005, 336(4), 1081-6. 28. Urothelial Cancer Matsui et al., Oncogene, (2008) 27, 4603-4614).

The following documents are directed to triptolide and diseases other than cancer (1. Multiple diseases: D Qui et al., Drug R & D, 2003, 4, 1-16.

2. Organ transplantation: Chen, Leukemia and Lymphoma, 2001, 42, 253-256.

3. Kidney transplant: Zhang et al., Journal of Ethnopharmacology, 2009, 125(1), 141-46. 4. Transplantation graft survival (skin): Yang et al. Int. J. Immunophamac., 1992, 14, 963-969. 5. Graft-Versus-Host disease: Chen et al., Transplantation, 2000, 70, 1442-1447. 6. Inflammatory and autoimmune diseases: P. E. Lipsky et al., Seminars in Arthritis and Rheumatism, 1997, 5, 713-723. 7. Autoimmune encephalomyelitis: Kizelsztein et al. Journal of
Neuroimmunology, 2009, 217, 28-37. 8. Cerebral ischemia/reperfusion injury: Wei et al., Neural Regeneration Research, 2007. 9. Colitis: Wei et al., Clin. Immunol. 2008, 129, 211-218. 10. Contraception in males and females: Hikim et al., Journal of Andrology, 2000, 21, 431-437., Huynh et al., Journal of Andrology, 2000, 21, 689-699., Wang et al., Asian Journal of Andrology, 1999, 1, 121-125., Lue et al., Journal of Andrology, 1998, 19, 479-486. 11. Corneal ulcer: Lu et al. Investigative Ophthalmology and Visual Science. 2006, 47, 3796-3800. 12. Lung inflammation: Krishna, et al., 2001, Am. J. Pathol., 2001, 158(3), 997-1004. 13. Nephritis: Tao et al., Arthritis Rheum. 2008, 58(6), 1774-83. 14. Parkinsonism and neuroprotection: Zhou et al., Neurobiology of Disease, 2005, 18, 441-449. 15. Polycystic kidney disease (PKD): Leuenroth et al., PNAS, 2007, 104, 4389-4394. 16. Spinal cord repair: Su et al., Glia 2010, 58, 901-915. 17. Stent coating: Q. Luo 2005, Patent application 20050043788).

The invention will now be illustrated by the following non-limiting Examples.

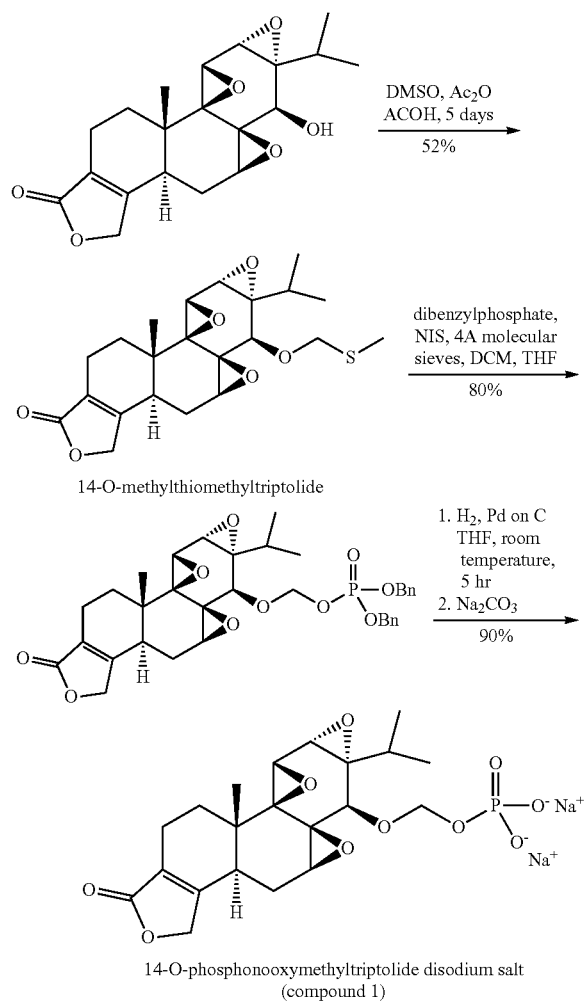

14-O-methylthiomethyltriptolide

14-O-phosphonooxymethyltriptolide disodium salt (compound 1)

Example 1

Synthesis of 14-O-phosphonooxymethyltriptolide disodium salt (compound 1)

To a solution of 14-O-phosphonooxymethyltriptolide dibenzyl ester (50 mg, 0.08 mmol) in tetrahydrofuran (5 mL) was added palladium on carbon (10%, 10 mg). The mixture was stirred at room temperature under hydrogen (1 atm) for a period of 3 hours. The catalyst was removed by filtration through CELITE™, and the filtrate was treated with a solution of sodium carbonate hydrate (8.9 mg in 3 mL water, 0.076 mmol). The tetrahydrofuran was evaporated under reduced pressure and the residual water solution was extracted with ether (3×3 mL). The aqueous layer was evaporated to dryness and the resulting solid was dried overnight in vacuo, washed with ether and again dried in vacuo to provide 14-O-phosphonooxymethyltriptolide disodium salt (35 mg, 90% yield) as a white powder. $^1$H NMR (400 MHz, D$_2$O) δ 0.81 (d, 3H, J=6.8 Hz), 1.00 (d, 3H, J=6.8 Hz), 1.03 (s, 3H), 1.35 (m, 1H), 1.50 (m, 1H), 2.00 (dd, 1H, J$_1$=14.7 and J$_2$=13.4 Hz), 2.08-2.61 (m, 4H), 2.85 (m, 1H), 3.63 (d, 1H, J=5.5 Hz), 3.81 (d, 1H, J=3.1 Hz), 3.86 (s, 1H), 4.12 (d, 1H, J=3.1 Hz), 4.92 (m, 2H), 5.07 (m, 2H) ppm; $^{13}$C NMR (100 MHz, D$_2$O) δ 12.9, 16.0, 16.3, 16.5, 22.3, 25.5, 28.9, 35.2, 39.8, 55.4, 56.1, 61.0, 61.5, 65.1, 65.5, 71.9, 77.6, 91.7, 123.8, 164.2, 177.3 ppm; HRMS calculated for (C$_{21}$H$_{26}$O$_{10}$P) required m/z [M+1]$^+$ 469.1264. Found m/z 469.1267.

Preparation of 14-O-phosphonooxymethyltriptolide dibenzyl ester

Step 1:

A solution of triptolide (100 mg, 0.29 mmol) in acetic acid (5 mL, 87.5 mmol) and acetic anhydride (1 mL, 10.5 mmol) in DMSO (1.5 mL, 21.4 mmol) was prepared and stirred at room temperature for a period of 5 days to yield 14-O-methylthiomethyltriptolide intermediate. The reaction mixture was then poured into water (100 mL) and neutralized with solid NaHCO$_3$, added in portions. The mixture was extracted with ethyl acetate (50 mL×3), and the combined organic extract was dried over anhydrous sodium sulfate and concentrated to furnish the product as an oil. Flash silica gel column chromatography (3:2 hexane/ethyl acetate) provided 14-O-methylthiomethyltriptolide in 52% (60 mg) as a white foam. $^1$H NMR (400 MHz, CDCl$_3$) δ 0.82 (d, 3H, J=6.8 Hz), 1.00 (d, 3H, J=6.8 Hz), 1.09 (s, 3H), 1.20 (m, 1H), 1.59 (m, 1H), 1.93 (dd, 1H, J$_1$=14.7 and J$_2$=13.4 Hz), 2.19 (s, 3H), 2.10-2.42 (m, 4H), 2.68 (m, 1H), 3.24 (d, 1H, J=5.5 Hz), 3.51 (d, 1H, J=3.1 Hz), 3.67 (s, 114), 3.79 (d, 1H, J=3.1 Hz), 4.68 (m, 2H), 4.93 (d, 1H, J=11.8 Hz), 5.07 (d, 1H, J=11.8 Hz) ppm; $^{13}$C NMR (100 MHz, CDCl$_3$) δ 13.6, 14.8, 16.8, 17.0, 17.1, 23.4, 26.3, 29.5, 35.8, 40.4, 54.5, 55.0, 58.0, 61.5, 63.9, 64.4, 69.9, 75.8, 76.7, 125.5, 160.2, 173.2 ppm; HRMS calculated for (C$_{22}$H$_{28}$O$_6$SNa) required m/z [M+Na]$^+$ 443.1505. Found m/z 443.1507.

Step 2:

A solution of 14-O-methylthiomethyltriptolide (50 mg, 0.12 mmol) in dry methylene chloride (2 mL) under an N$_2$ atmosphere was combined with powdered activated 4 Å molecular sieves (50 mg), followed by the addition of a mixture of dibenzylphosphate (40 mg, 0.14 mmol) and N-iodosuccinimide (32 mg, 0.14 mmol) in tetrahydrofuran (2 mL). The reaction mixture was stirred at room temperature for a period of 5 hours, filtered, and diluted with methylene chloride (20 mL). The resulting solution was washed with a solution of sodium thiosulfate (2 mL, 1M solution), a saturated solution of sodium bicarbonate, brine, dried over a sodium sulfate, filtered, and concentrated in vacuo. The oily residue was purified by silica gel flash chromatography (1:2 hexane/ethyl acetate) to give 14-O-phosphonooxymethyl-triptolide dibenzyl ester (62 mg, 80% yield) as a white foam. $^1$H NMR (400 MHz, CDCl$_3$) δ 0.72 (d, 3H, J=6.8 Hz), 0.89 (d, 3H, J=6.8 Hz), 1.05 (s, 3H), 1.27 (m, 1H), 1.48 (m, 1H), 1.82 (dd, 1H, J$_1$=14.7 and J$_2$=13.4 Hz), 2.03-2.35 (m, 4H), 2.64 (m, 1H), 3.14 (d, 1H, J=5.5 Hz), 3.46 (d, 1H, J=3.1 Hz), 3.65 (s, 1H), 3.76 (d, 1H, J=3.1 Hz), 4.65 (m, 2H), 5.02 (m, 4H), 5.27 (m, 1H), 5.47 (m, 1H), 7.34 (m, 10H) ppm; $^{13}$C NMR (100 MHz, CDCl$_3$) δ 13.6, 16.8, 17.0, 23.3, 26.2, 29.62, 29.67, 35.7, 40.3, 54.7, 55.2, 59.3, 61.1, 63.6, 64.0, 69.36, 69.39, 69.42, 69.45, 69.9, 78.2, 92.9, 93.0, 125.5, 127.9, 128.0, 128.6, 135.5, 135.6, 160.1, 173.2 ppm; HRMS calculated for (C$_{35}$H$_{39}$O$_{10}$PNa) required m/z [M+Na]$^+$ 673.2179. Found m/z 673.2176.

portions over 20 min, and then the mixture was stirred at 0° C. for 1 h and thereafter at room temperature for 1 h. The mixture was diluted with ethyl acetate and washed with 10% Na$_2$CO$_3$ and then brine. The organic phase was dried over MgSO$_4$, filtered, and evaporated. The residue was purified by silica gel flash chromatography (1:1 hexane/ethyl acetate) to furnish 14-O-methylthiomethyltriptolide (63 mg, 54% yield) as a colorless powder.

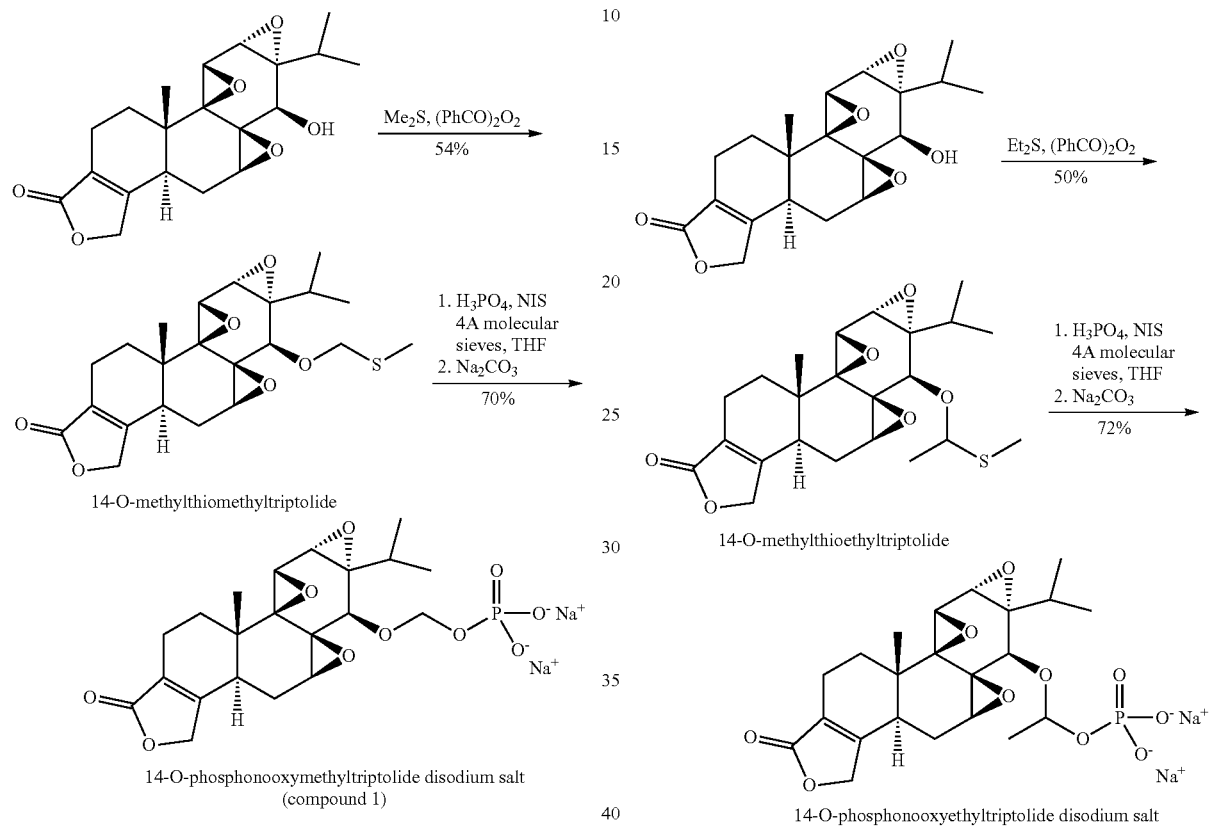

Example 2

Synthesis of 14-O-phosphonooxymethyltriptolide disodium salt (compound 1)

To a solution containing 14-O-methylthiomethyltriptolide (50 mg, 0.12 mmol), phosphoric acid (82 mg, 0.84 mmol), and molecular sieves (4 Å, 0.45 g) in THF (10 mL) at 0° C. was added N-iodosuccinimide (41 m g, 0.18 mmol), and the mixture was stirred at room temperature for 1 h. The reaction mixture was filtered through Celite, and the solids were washed with THF. The filtrate was treated with 1 M Na$_2$S$_2$O$_3$ until it was colorless and the filtrate was treated with a solution of sodium carbonate (13 mg in 3 mL water, 0.12 mmol). The filtrate was evaporated under reduced pressure and the residual water solution was extracted with ether (3×3 mL). The aqueous layer was evaporated to dryness and the resulting residue was purified by chromatography (C 18), eluting with a gradient of 0-100% methanol in water to give 14-O-phosphonooxymethyltriptolide disodium salt (43 mg, 70% yield) as a colorless powder.

Preparation of 14-O-methylthiomethyltriptolide.

To a solution of triptolide (100 mg, 0.28 mmol) and methyl sulfide (0.16 mL, 2.24 mmol) in acetonitrile (10 mL) at 0° C. was added benzoyl peroxide (0.27 g, 1.12 mmol) in four equal

Example 3

Synthesis of 14-O-Phosphonooxyethyltriptolide disodium salt

To a solution containing 14-O-methylthioethyltriptolide (52 mg, 0.12 mmol), phosphoric acid (82 mg, 0.84 mmol), and molecular sieves (4 Å, 0.45 g) in THF (10 mL) at 0° C. was added N-iodosuccinimide (41 mg, 0.18 mmol), and the mixture was stirred at room temperature for 1 h. The reaction mixture was filtered through Celite, and the solids were washed with THF. The filtrate was treated with 1 M Na$_2$S$_2$O$_3$ until it was colorless and the filtrate was treated with a solution of sodium carbonate (13 mg in 3 mL water, 0.12 mmol). The filtrate was evaporated under reduced pressure and the residual water solution was extracted with ether (3×3 mL). The aqueous layer was evaporated to dryness and the resulting residue was purified by chromatography (C18), eluting with a gradient of 0-100% methanol in water to give 14-O-phosphonooxyethyltriptolide disodium salt (46 mg, 72% yield) as a colorless powder. $^1$H NMR (400 MHz, D$_2$O) δ 0.68 (d, 3H, J=6.8 Hz), 0.70 (d, 3H, J=6.8 Hz), 1.03 (s, 3H), 1.21 (m, 1H), 1.57 (d, 3H, J=5.3 Hz), 1.58 (m, 1H), 1.94 (dd, 1H, J$_1$=14.7 and J$_2$=13.4 Hz), 2.08-2.61 (m, 4H), 2.62 (m, 1H), 3.27 (d, 1H, J=5.5 Hz), 3.45 (d, 1H, J=3.1 Hz), 3.72 (d, 1H, J=3.1 Hz), 3.79 (s, 1H), 4.63 (m, 2H), 6.43 (q, 1H, J=5.3 Hz) ppm; $^{13}$C NMR (100 MHz, D$_2$O) δ 13.5, 16.9, 17.0, 17.1, 21.4, 23.5, 26.8, 29.5, 35.9, 40.3, 54.0, 55.1, 59.4, 61.2, 63.6, 64.2, 69.8, 75.8, 76.5, 91.6, 125.6, 164.2, 177.2 ppm; HRMS calculated for (C$_{22}$H$_{28}$O$_{10}$P) required m/z [M+1]$^+$483.1137. Found m/z 483.1134.

Preparation of 14-O-methylthioethyltriptolide.

To a solution of triptolide (100 mg, 0.28 mmol) and ethyl sulfide (0.24 mL, 2.24 mmol) in acetonitrile (10 mL) at 0° C. was added benzoyl peroxide (0.27 g, 1.12 mmol) in four equal portions over 20 min, and then mixture was stirred at 0° C. for 1 h and then at room temperature for 1 h. The mixture was diluted with ethyl acetate and washed with 10% Na$_2$CO$_3$ and then brine. The organic phase was dried over MgSO$_4$, filtered, and evaporated. The residue was purified by silica gel flash chromatography (1:1 hexane/ethyl acetate) to give 14-O-methylthioethyltriptolide (60 mg, 50% yield) as a colorless powder. $^1$H NMR (400 MHz, CDCl$_3$) δ 0.68 (d, 3H, J=6.8 Hz), 0.70 (d, 3H, J=6.8 Hz), 1.04 (s, 3H), 1.20 (m, 1H), 1.57 (d, 3H, J=5.3 Hz), 1.59 (m, 1H), 1.88 (dd, 1H, J$_1$=14.7 and J$_2$=13.4 Hz), 2.19 (s, 3H), 2.06-2.27 (m, 4H), 2.62 (m, 1H), 3.24 (d, 1H, J=5.5 Hz), 3.42 (d, 1H, J=3.1 Hz), 3.70 (d, 1H, J=3.1 Hz), 3.73 (s, 1H), 4.61 (m, 2H), 5.02 (q, 1H, J=5.3 Hz) ppm; $^{13}$C NMR (100 MHz, CDCl$_3$) 13.6, 14.8, 16.9, 17.0, 17.1, 21.0, 23.5, 26.4, 29.6, 35.8, 40.5, 54.0, 55.2, 59.4, 61.3, 63.7, 64.2, 69.9, 75.8, 76.7, 125.6, 160.2, 173.2 ppm; HRMS calculated for (C$_{23}$H$_{30}$O$_6$SNa) required m/z [M+Na]$^+$457.1763. Found m/z 457.1765.

Example 4

Synthesis of 14-O-Phosphonooxypropyltriptolide disodium salt

To a solution containing 14-O-methylthiopropyltriptolide (54 mg, 0.12 mmol), phosphoric acid (82 mg, 0.84 mmol), and molecular sieves (4 Å, 0.45 g) in THF (10 mL) at 0° C. was added N-iodosuccinimide (41 mg, 0.18 mmol), and the mixture was stirred at room temperature for 1 h. The reaction mixture was filtered through Celite, and the solids were washed with THF. The filtrate was treated with 1 M Na$_2$S$_2$O$_3$ until it was colorless and the filtrate was treated with a solution of sodium carbonate (13 mg in 3 mL water, 0.12 mmol). The filtrate was evaporated under reduced pressure and the residual water solution was extracted with ether (3×3 mL). The aqueous layer was evaporated to dryness and the resulting residue was purified by chromatography (C18), eluting with a gradient of 0-100% methanol in water to provide 14-O-phosphonooxypropyltriptolide disodium salt (43 mg, 65% yield) as a colorless powder. $^1$H NMR (400 MHz, D$_2$O) δ 0.66 (d, 3H, J=6.8 Hz), 0.68 (d, 3H, J=6.8 Hz), 0.99 (t, 3H, J=5.3 Hz), 1.03 (s, 3H), 1.20 (m, 1H), 1.53 (m, 1H), 1.90 (dd, 1H, J$_1$=14.7 and J$_2$=13.4 Hz), 2.04-2.66 (m, 4H), 2.65 (m, 3H), 3.27 (d, 1H, J=5.5 Hz), 3.49 (d, 1H, J=3.1 Hz), 3.71 (d, 1H, J=3.1 Hz), 3.78 (s, 1H), 4.69 (m, 2H), 6.31 (q, 1H, J=5.3 Hz) ppm; $^{13}$C NMR (100 MHz, D$_2$O) δ 7.55, 13.5, 16.2, 16.9, 17.2, 20.8, 23.2, 26.1, 28.4, 34.7, 38.5, 54.1, 55.0, 59.0, 61.3, 62.5, 63.9, 68.5, 75.4, 76.4, 91.9, 125.7, 160.1, 174.5 ppm; HRMS calculated for (C$_{23}$H$_{29}$O$_{10}$P) required m/z [M+1]$^+$ 497.1294. Found m/z 497.1292

Preparation of 14-O-methylthiopropyltriptolide.

To a solution of triptolide (100 mg, 0.28 mmol) and propyl sulfide (0.32 mL, 2.24 mmol) in acetonitrile (10 mL) at 0° C. was added benzoyl peroxide (0.27 g, 1.12 mmol) in four equal portions over 20 min, and the mixture was stirred at 0° C. for 1 h and then at room temperature for 1 h. The mixture was diluted with ethyl acetate and washed with 10% Na$_2$CO$_3$ and then brine. The organic phase was dried over MgSO$_4$, filtered, and evaporated. The residue was purified by silica gel flash chromatography (1:1 hexane/ethyl acetate) to give 14-O-methylthiopropyltriptolide (60 mg, 48% yield) as a colorless powder. $^1$H NMR (400 MHz, CDCl$_3$) δ 0.65 (d, 3H, J=6.8 Hz), 0.67 (d, 3H, J=6.8 Hz), 0.99 (t, 3H, J=5.3 Hz), 1.01 (s, 3H), 1.20 (m, 1H), 1.59 (m, 1H), 1.88 (dd, 1H, J$_1$=14.7 and J$_2$=13.4 Hz), 2.18 (s, 3H), 2.01-2.26 (m, 4H), 2.62 (m, 3H), 3.24 (d, 1H, J=5.5 Hz), 3.42 (d, 1H, J=3.1 Hz), 3.70 (d, 1H, J=3.1 Hz), 3.73 (s, 1H), 4.61 (m, 21-1), 5.03 (q, 1H, J=5.3 Hz) ppm; $^{13}$C NMR (100 MHz, CDCl$_3$) δ 7.68, 13.5, 14.6, 16.2, 17.0, 17.2, 21.4, 23.2, 26.1, 28.9, 34.7, 39.5, 54.1, 55.6, 59.0, 61.3, 63.5, 64.0, 69.5, 75.1, 76.4, 125.1, 160.9, 173.5 ppm; HRMS calculated for (C$_{24}$H$_{32}$O$_6$SNa) required m/z [M+Na]$^+$ 471.1920. Found m/z 471.1918.

Example 5

Chemical Properties of the Compounds of Formula I

The chemical properties of the compounds of the invention were evaluated. The aqueous solubility and chemical stability of the was measured. Using a solution of the compound of Example 1 with pH adjusted to 7.4, solubility at room temperature was determined to be 61.4 mg/mL. Stability of the compounds of the invention were evaluated in Tris buffer (pH 7.4) and Borate buffer (pH 7.4) solutions at room temperature. After a period of 1 (one) month, no degradation of the

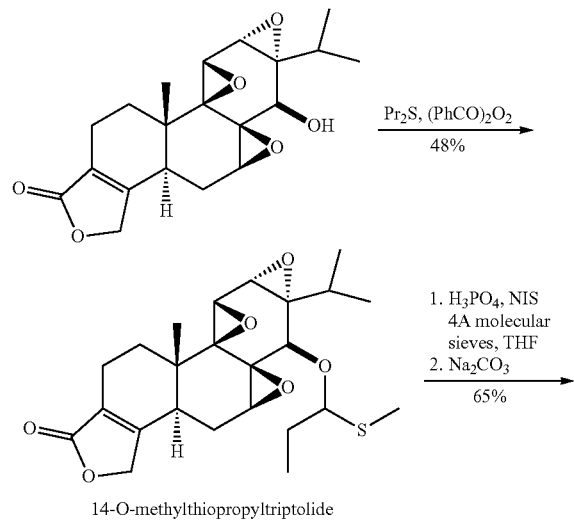

14-O-methylthiopropyltriptolide

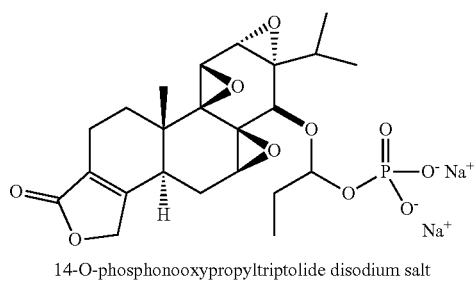

14-O-phosphonooxypropyltriptolide disodium salt compound of Example 1 was observed. The results are summarized in the following table.

TABLE 1

Physiochemical Properties of Compounds of Formula I

| Compound | Solubility (mg/mL) Tris buffer, room temp | Chemical Stability (t½) Tris buffer, room temp | Chemical Stability (t½), Borate buffer, room temp. | Enzymatic Hydrolysis (t½), Alkaline Phosphatase, 37° C. |
|---|---|---|---|---|
| Compound of Example 1/2 | 61.4 | * | * | 2 min. |
| Compound of Example 3 | >50 | * | * | 9 min. |
| Compound of Example 4 | >50 | * | * | 17 min. |

* No degradation observed after one month.

Example 6

In Vitro Enzymatic Conversion Compound 1

Compound 1 is converted into the active tritpolide form by action of the enzyme alkaline phosphatase. An in vitro experiment to study the bioconversion of the tritpolide prodrug compound of the invention was performed. In vitro bioconversion was simulated using alkaline phosphatase (from bovine intestinal mucosa, Type VII-S available from Sigma-Aldrich (St. Louis, Mo.) in glycine buffer (pH 9.8).

Alkaline phosphatases are a group of enzymes found primarily in the liver (isoenzyme ALP-1) and bone (isoenzyme ALP-2), with small amounts being produced by the cellular lining of the small intestine (isoenzyme ALP-3), placenta and kidneys. Alkaline phosphatases split off phosphorous to create an alkaline pH. Other enzymes in addition to alkaline phosphatase may contribute to in vivo hydrolysis as well.

Figure 3:
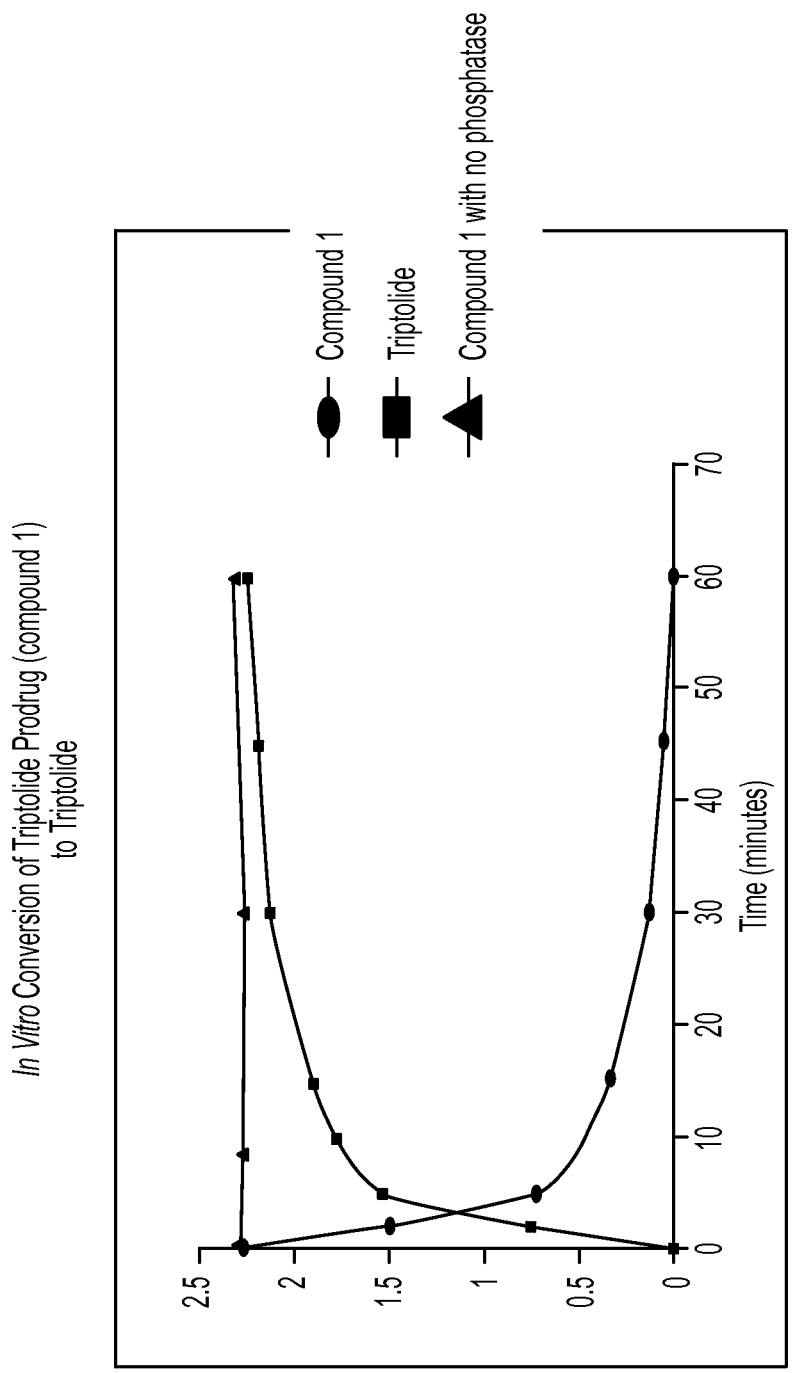
FIG. 3 illustrates the in vitro enzymatic conversion of the triptolide prodrug (compound 1 to triptolide.

From FIG. 3, it can be seen that the decreasing amounts of the triptolide prodrug form were coincident with the proportionate increasing amounts of active form released triptolide. Furthermore, it was observed that the conversion occurred over a relatively short time period, with the majority of conversion taking place over the initial time period of 10 minutes.

The first order degradation constant was calculated by fitting the remaining concentration versus the incubation time. The degradation half-life (t ½) of compound 1 was determined to be 2 minutes.

Example 7

Comparative In Vitro Cell Viability Study

An experiment was conducted to evaluate comparative in vitro cell viability using triptolide, the prodrug of triptolide (compound 1), and control (without triptolide or the prodrug form). Cell viability was determined using the Dojindo Cell Counting Kit-8 (available from Dojindo Laboratories, Rockville, Md.). Pancreatic cancer cells were seeded into a 96 well plate at $2\times10^3$ cells per well and allowed to adhere overnight. The cells were then treated with the prodrug triptolide (compound 1), of the invention and native triptolide at various concentrations for periods of 24 hours and 48 hours. Tetrazolium substrate (10 µl) was added to each well of the plate. The plates were incubated at 37° C. for 1 hour, after which absorbance at 460 nm was measured. Each experiment was performed in triplicate and repeated three independent times.

Figure 4:
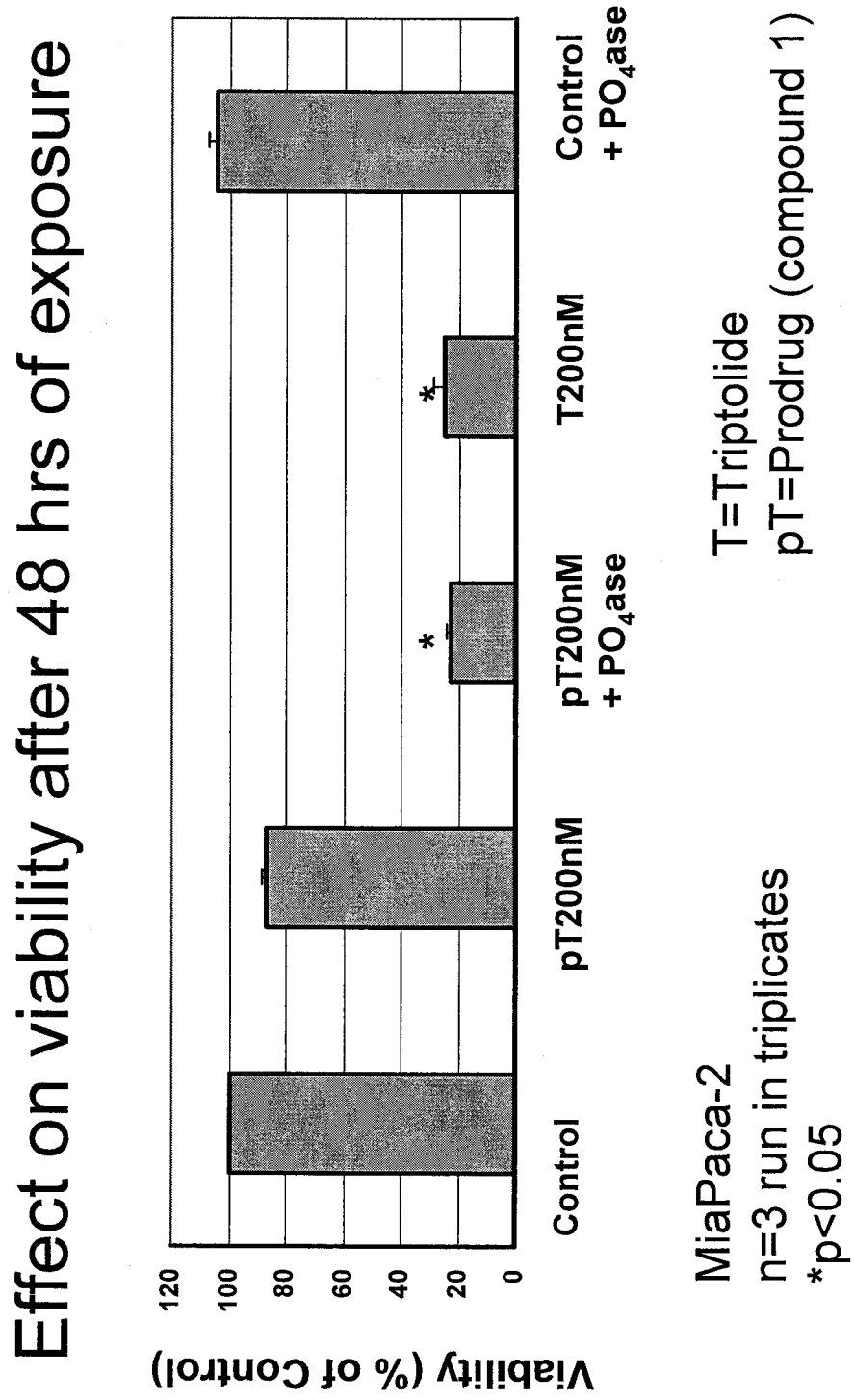
FIG. 4 illustrates the comparative effects of triptolide and the triptolide prodrug (compound 1) on MiaPaca-2 cell viability in vitro at 48 hours.
Figure 5:
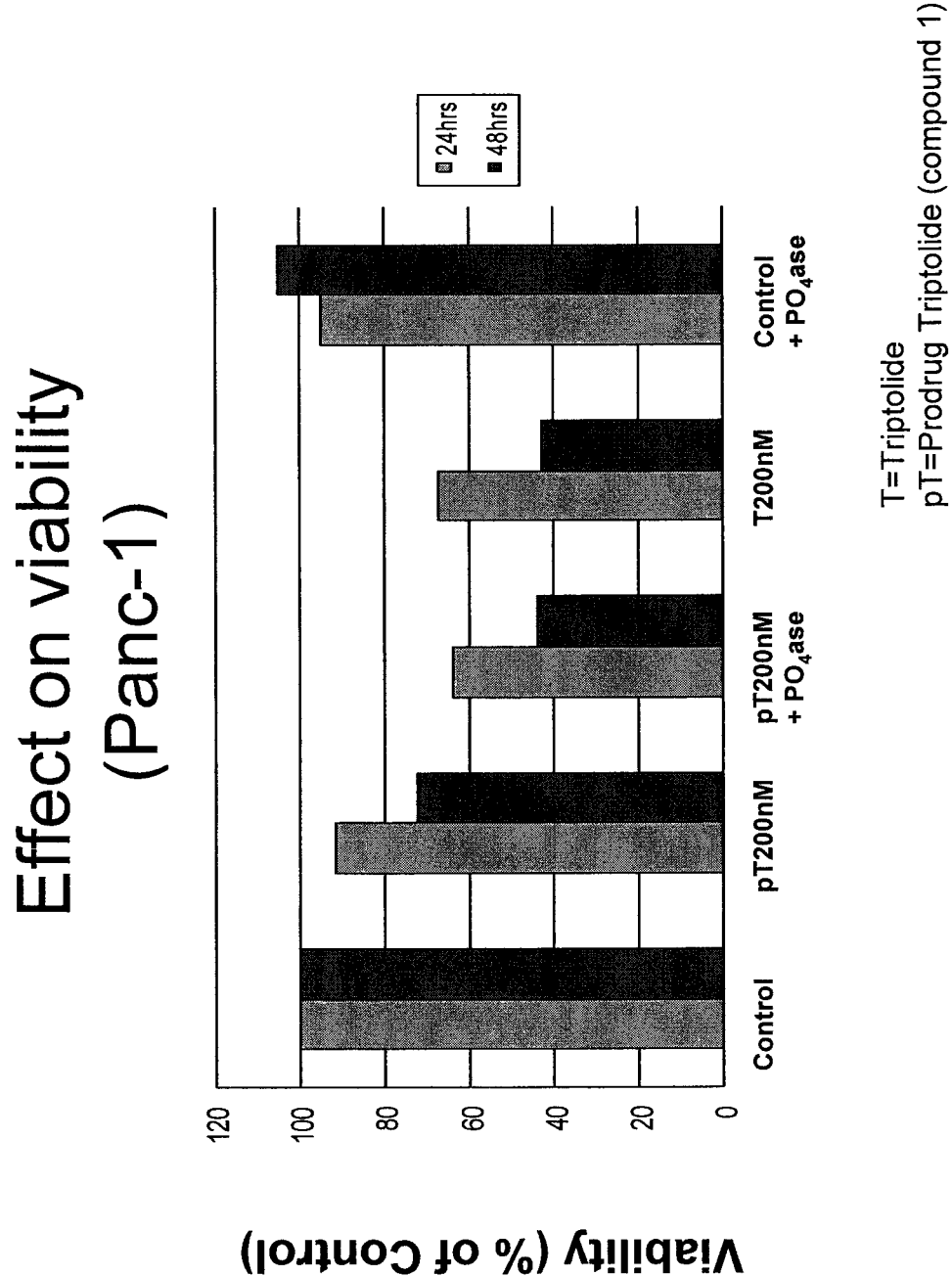
FIG. 5 illustrates the comparative effects of triptolide and the triptolide prodrug (compound 1) upon Panc-1 cell viability in vitro at both 24 hours and 48 hours.
Figure 6:
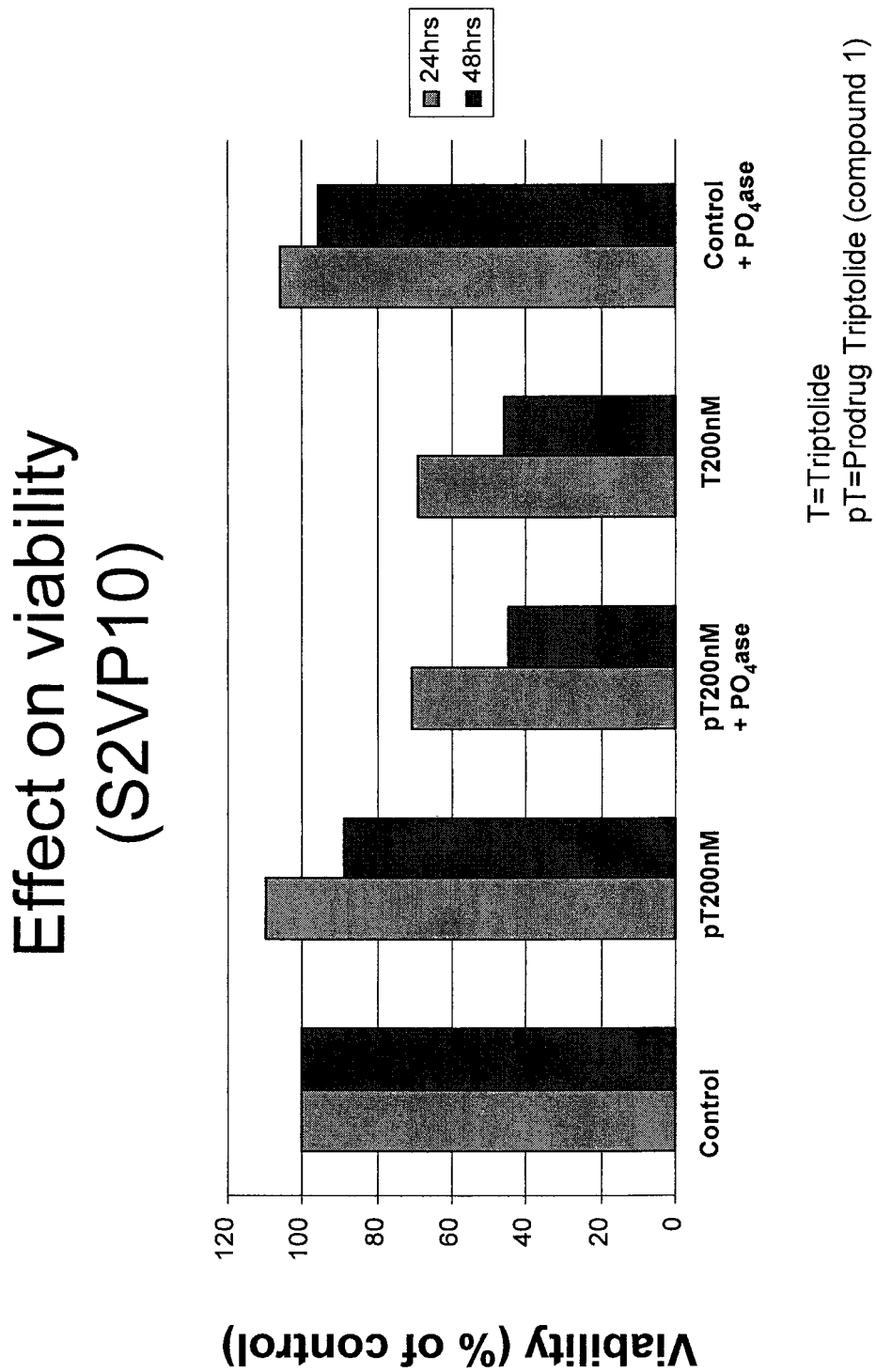
FIG. 6 illustrates the comparative effects of triptolide and triptolide prodrug (compound 1) on S2VP10 cell viability in vitro at 24 hours and 48 hours.
Figure 7:
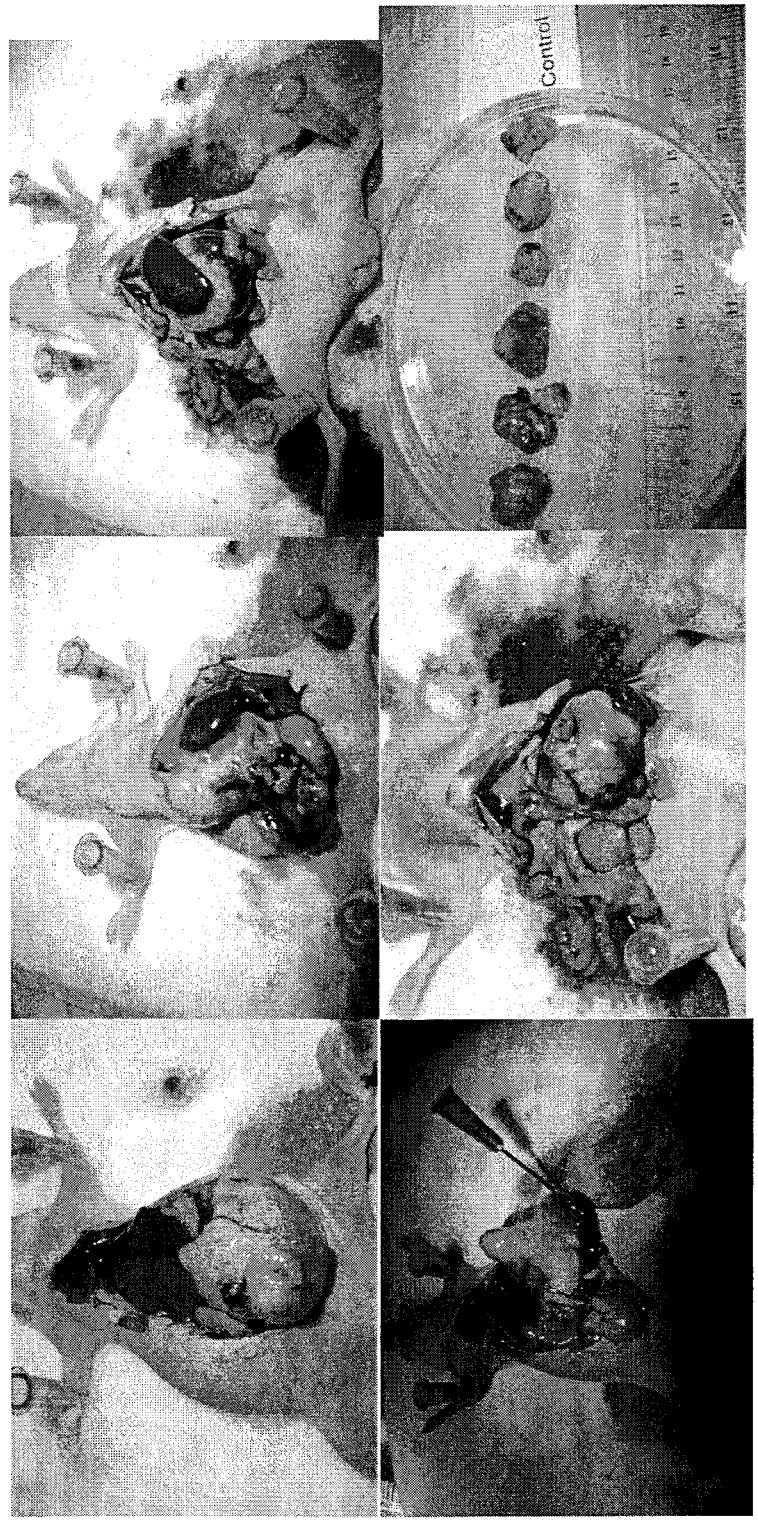
FIG. 7 illustrates tumor growth in a control group of mice with five photographs in situ and one photograph of tumors ex vivo.

The effect of the compound 1 and triptolide on the viability of pancreatic cancer cells was observed following incubation in medium containing the prodrug tritpolide at concentrations ranging from 50 to 200 nmol/L at 24 hours and 48 hours. The data was collected and converted into the charts of FIG. 4 (Cell Viability Mia-Paca at 48 hours), FIG. 5 (Cell Viability Panc-1 at 24 and 48 hours) and FIG. 6 (Cell Viability S2VP10 at 24 and 48 hours).

As can be seen from each of the above data and figures, the presence of the triptolide prodrug and alkaline phosphatase and native form triptolide significantly reduced pancreatic cell viability in vitro in a time- and dose-dependent manner.

Example 8

Comparative In Vivo Study of Compound 1 on Mice

Thirty nude mice of the strain athymic nu/nu were obtained from National Cancer Institute (NCI) (Rockville, Md.) and kept in a RAR facility. The mice were anaesthetized in accordance with the recommendations of the RAR facility using ketamine 75-200 mg/kg and xylazine 4-8 mg/kg. A small incision 3 mm was made on the left side of the abdominal wall and the spleen was pulled out with forceps far enough to expose and access the pancreas. MiaPaca-2 cell medium was prepared and kept on ice until delivery into the mice. Into each of the mice, 1 million MiaPaca-2 cells suspended in MATRIGEL™ (available from Becton-Dickinson Corporation, Franklin Lakes, N.J.) was injected into the tail of the pancreas (identified by its anatomical attachment with the spleen) using a Hamilton syringe. Following delivery of the cells, the syringe was held steady for an additional 5-10 seconds to permit the MATRIGEL™ to set. The spleen was replaced back into the abdominal cavity, and the abdominal wall was closed by vicryl suture in a continuous manner. The skin was apposed and closed using wound clips. The mice were then transferred to a heating pad until fully recovered before being returned to the cage. Post-operative pain medication (buprenonorphine 0.1 mg/kg) was administered intraperitoneally immediately after full recovery from anaesthesia to prevent respiratory depression and then administered every 12 hours for 2 days. The wound clips were removed from the mice after 7 days of surgery.

The mice were then randomized into 3 groups, each group having 10 mice. The groups were as follows: control group, triptolide group and the triptolide prodrug (compound 1) group. The control group consisted of mice that were injected intraperitoneally with vehicle DMSO. The triptolide group subjects were injected with 0.2 mg/kg of triptolide dissolved in DMSO and diluted with phosphate buffered saline to a volume of 100 µl, the intraperitoneal injections being daily over a period of 60 days. The compound 1 subjects were intraperitoneally injected daily for 60 days with 0.28 mg/kg of the compound dissolved in phosphate buffered saline diluted to a volume of 100 µl.

The mice were euthanized under anaesthesia at the conclusion of the 60 day treatments. Samples were collected (blood, lung, spleen, liver, kidneys and tumor tissue), and tumor volume and weight were measured and compared among the different groups. Observations were made on the loco-regional growth and cancer growth.

Figure 8:
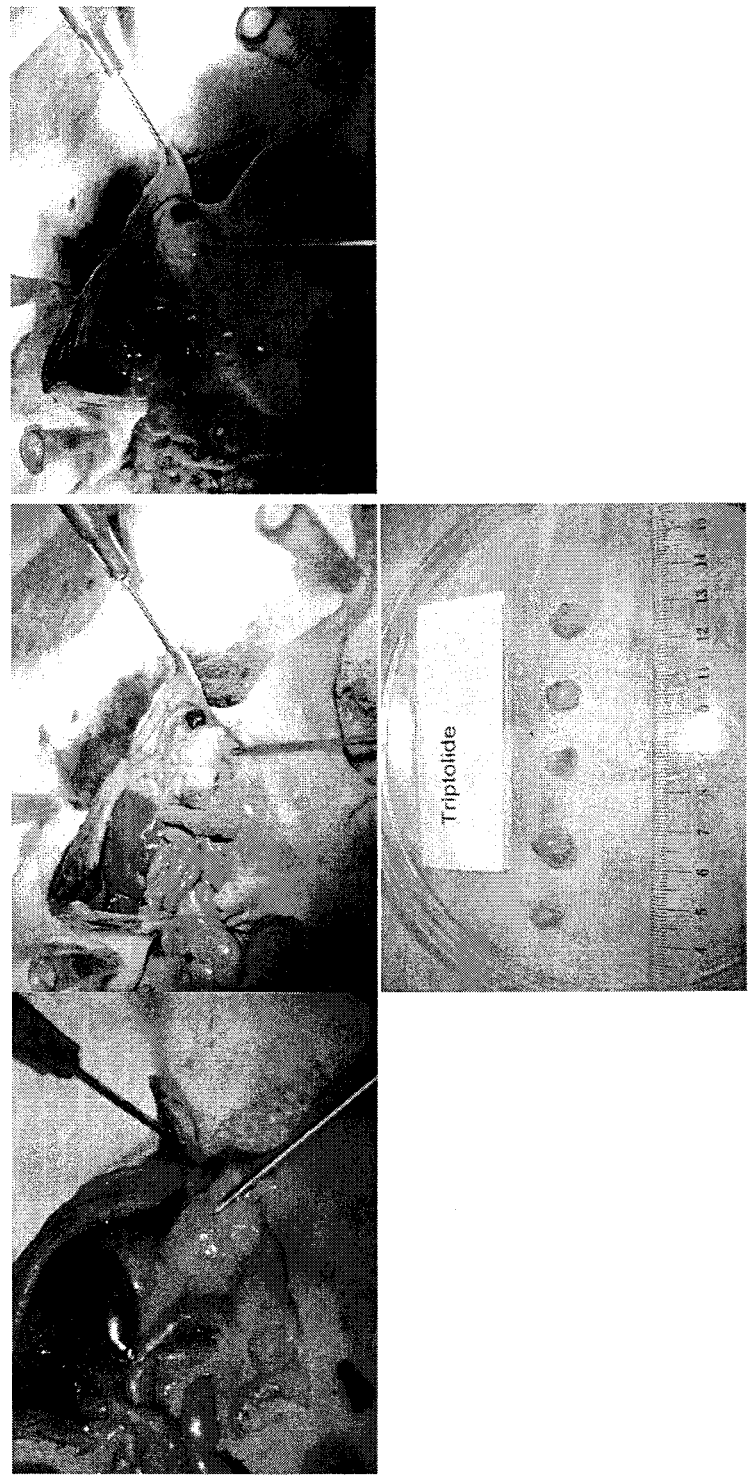
FIG. 8 illustrates tumor growth in a triptolide group of mice with three photographs in situ and one photograph of tumors ex vivo.
Figure 9:
FIG. 9 illustrates tumor growth in a triptolide prodrug (compound 1) group of mice with four photographs in situ and one photograph of tumors ex vivo.
Figure 10:
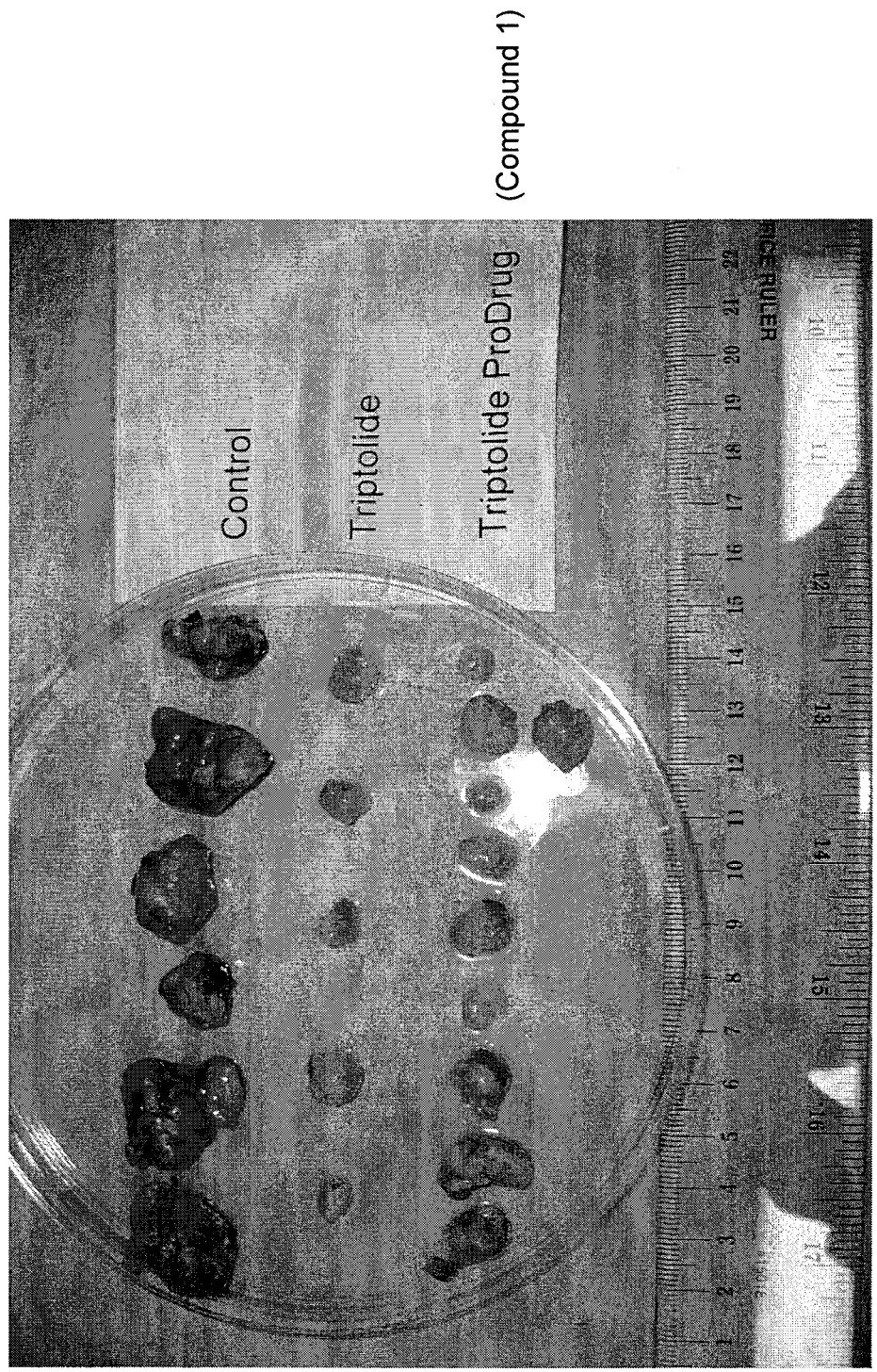
FIG. 10 is a photograph of the ex vivo tumor collection from the in vivo experiment showing comparative tumor sizes for the control group, triptolide group and the triptolide prodrug (compound 1).
Figure 11:
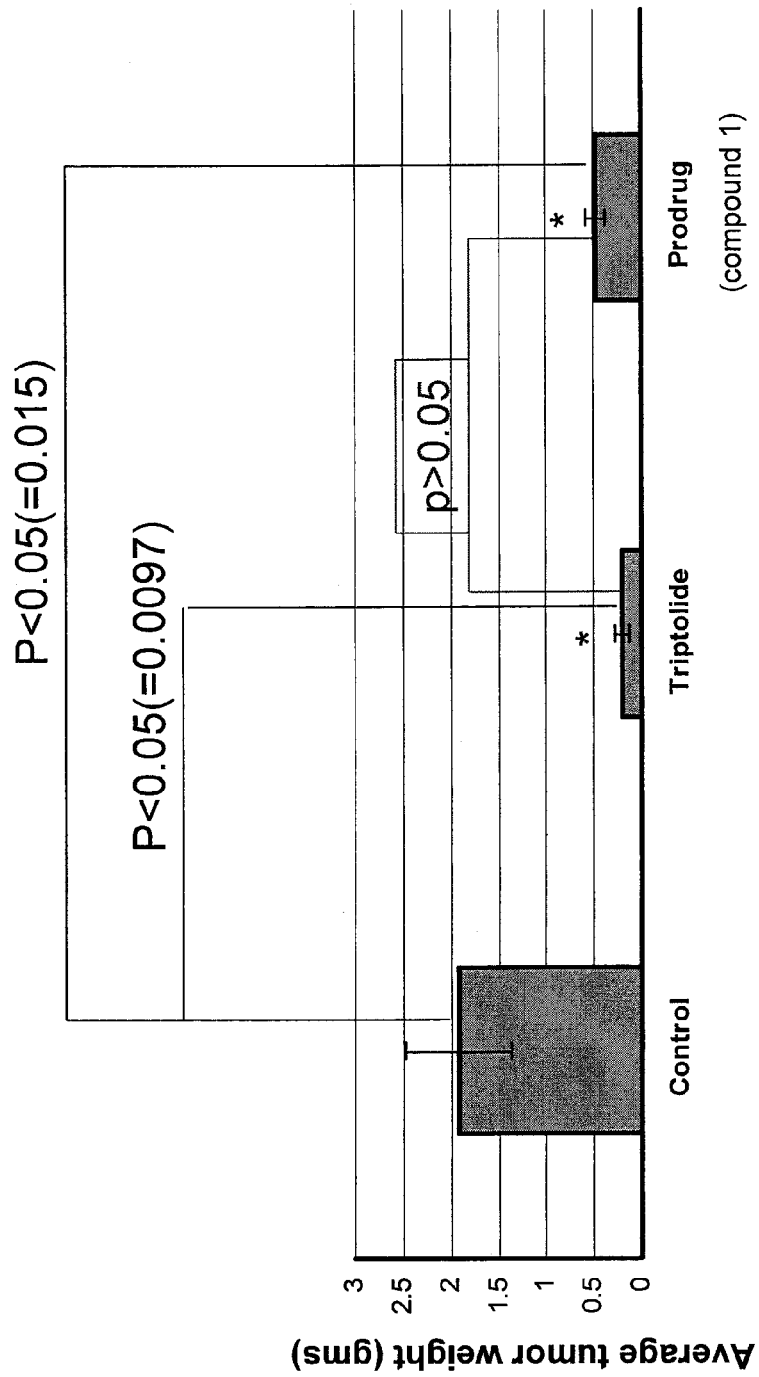
FIG. 11 illustrates comparative tumor weight (g) for the tumors of the control group, triptolide group and the triptolide prodrug (compound 1) group of mice from the in vivo experiment.

FIG. 8 (photographs from the control group), FIG. 9 (photographs of the triptolide group) and FIG. 10 (photographs from the triptolide prodrug of Example 1 group), are a collection of photographs showing final tumor growth from each of the groups of mice of the in vivo experiment. FIG. 11 is a photograph of the collection of excised tumors taken from mice from each of groups and aligned alongside on a row corresponding to each group.

Figure 12:
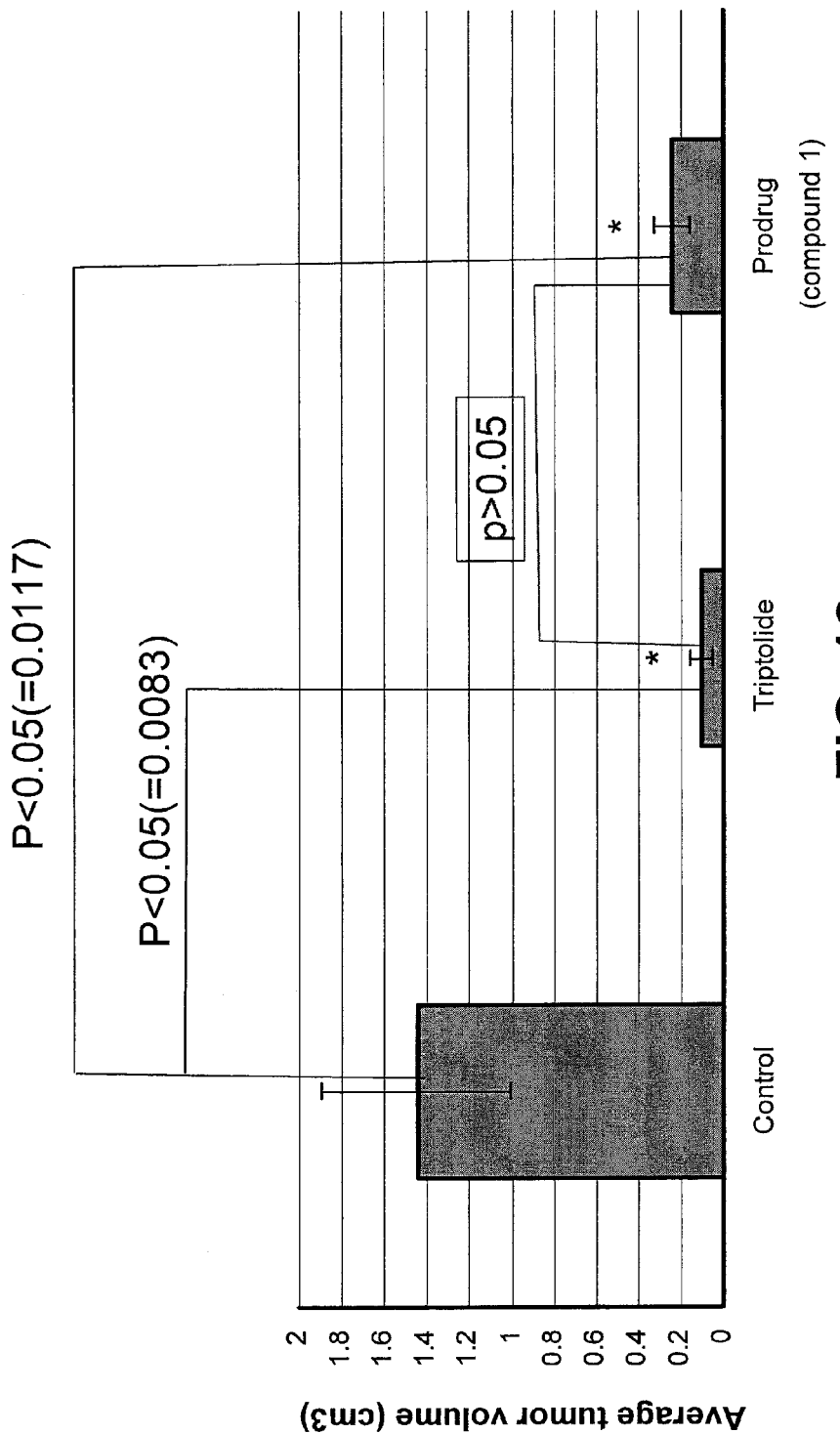
FIG. 12 illustrates comparative tumor volume (cm³) for the tumors of the control group, triptolide group and the triptolide prodrug (compound 1) group of mice from the in vivo experiment.

The tumors excised from the untreated control group were considerably larger at 60 days than those excised from the other two groups, showing continued aggressive growth of the pancreatic tumor cells. In contrast, the compound of Example 1 group exhibited considerable pancreatic tumor growth inhibition as compared to the untreated control group, and substantial effective tumor cell inhibition as compared to native form triptolide. Referring now to FIG. 11 and FIG. 12, which show comparative tumor weight and tumor volume between the three groups respectively, the control group tumors were considerably larger both in terms of weight (g) and volume ($cm^3$) as compared to the triptolide and triptolide prodrug (compound 1) group tumor data.

Thus, when administered to a living mammal in vivo, the triptolide prodrug compound of the invention can effectively inhibit tumor growth and inhibitory effect effectiveness comparable to native non-prodrug form triptolide. As can be seen from the above data and figures, the pancreatic cancer tumor growth in the mice treated with native triptolide and triptolide prodrug (compound 1) for 60 days exhibited significantly reduced tumor volume as compared with the untreated control group. Furthermore, it was significant that in both the triptolide and triptolide prodrug group subjects, there was no apparent significant impact on body weight and no apparent signs of toxicity in the subjects. Thus, the compounds of the invention can provide tumor inhibition and inhibit cancer cell growth and in particular pancreatic cancer cell growth. Additionally, the compounds of the invention could also provide the basis for effective treatment to inhibit pancreatic cancer with low toxic side-effects in living mammals.

Example 9

Compound 1 Induced Tumor Regression in an Orthotopic Mouse Model of Pancreatic Cancer (60 Day Dosing Study)

MIA PaCa-2 cells ($1 \times 10^6$) were suspended in matrigel and injected into the tail of the pancreas of 4-6 week old female nude mice. Ten days post-cell implantation, mice were injected intraperitoneally with indicated concentrations of compound 1(0.1, 0.15, 0.3, 0.6 or 0.9 mg/kg) or 0.2 mg/kg Triptolide QD for 60d. Control mice were injected with saline BID. Treatment was stopped after 60d and mice were observed for another 28d before being sacrificed. Tumor samples, if any, were harvested from these mice, and tumor weight and volume measured. If tumor burden exceeded University of Minnesota animal care guidelines, mice were sacrificed at earlier time points and their tumors harvested. FIG. 13 illustrates the enhanced survival of mice treated with compound 1 and triptolide versus vehicle. FIG. 14 illustrates the enhanced survival of mice treated with compound 1 versus vehicle. FIG. 15 shows the decreased tumor burden, as measured by tumor volume or tumor weight, of compound 1 treated mice versus control mice.

Example 10

Compound 1 Induced Tumor Regression in an Orthotopic Mouse Model of Pancreatic Cancer (21 Day Dosing Study)

$1 \times 10^6$ Cells of S2013, a highly metastatic pancreatic cancer cell line, were suspended in matrigel and injected into the tail of the pancreas of 4-6 week old female nude mice. Seven days post-cell implantation, mice were injected intraperitoneally with 0.42 mg/kg of compound 1 for 21d. Treatment was stopped after 21d, and mice sacrificed. Tumor samples, if any, were harvested from these mice, and tumor weight and volume measured. If tumor burden exceeded University of Minnesota animal care guidelines, mice were sacrificed and their tumors harvested at an earlier time point. Control mice were injected with saline QD. FIG. 16 shows the decreased tumor burden, as measured by tumor volume or tumor weight, of compound 1 treated mice versus control mice.

Example 11

Compound 1 Induced Tumor Regression in a Subcutaneous Mouse Model of Cholangiocarcinoma SkChA-1cells ($5 \times 10^5$) were suspended in matrigel and injected subcutaneously into the left flank of 4-6 week old female nude mice. Seven days post-cell implantation, mice were injected intraperitoneally with 0.3 mg/kg of compound 1 BID for 25 days. Treatment was stopped at this point, and mice sacrificed. Tumor samples, if any, were harvested from these mice, and tumor weight and volume measured. If tumor burden exceeded University of Minnesota animal care guidelines, mice were sacrificed and their tumors harvested at an earlier time point. Control mice were injected with saline BID. FIG. 17 shows the decreased tumor burden, as measured by tumor volume or tumor weight, of compound 1 treated mice versus control mice.

Example 12

Triptolide Induced Tumor Regression in a Orthotopic Mouse Model of Neuroblastoma Neuroblastoma N2 cells ($1 \times 10^6$) were suspended in matrigel and injected into the left retroperitoneal space of 4-6 week old A/J immunocompetent mice. Three days post-cell implantation, mice were injected with 0.4 mg/kg of triptolide intraperitoneally for 21 days. Treatment was stopped at this point, and mice sacrificed. Tumor samples, if any, were harvested from these mice, and tumor weight and volume measured. If tumor burden exceeded University of Minnesota animal care guidelines, mice were sacrificed and their tumors harvested at an earlier time point. Control mice were injected with DMSO for 21 days. FIG. 18 shows the decreased tumor burden in the triptolide treated mice versus the control mice as measured by tumor volume and tumor mass.

Example 13

Triptolide Induced Cell Death and Capase-3 Activation in Neuroblastoma Cells

Neuroblastoma N2a and SKNSH cells were treated with triptolide, resulting in dose- and time-dependent cell killing in N2a, with more than 50% of cells killed with 62.5 nM triptolide at 24 hours and nearly 85% of cells killed with 250 nM triptolide at 48 hours (FIG. 19). To confirm the hypothesis that triptolide results in neuroblastoma cell death via an apoptotic pathway, caspase-3 activity was measured as a marker of apoptosis. In both cell lines, increases in caspase activity with higher doses of triptolide and longer duration of therapy. Triptolide treatment was associated with dose- and time-dependent increases in caspase-3 activity levels (FIG. 20).

These results suggest that triptolide-mediated cell death occurs via the induction of apoptosis.

Example 14

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 0.5 |
| Lactose | 77.5 |
| Povidone | 15.0 |
| Croscarmellose sodium | 12.0 |
| Microcrystalline cellulose | 92.5 |
| Magnesium stearate | 3.0 |
| | 185 |

| (ii) Tablet 2 | mg/tablet |
|---|---|
| Compound X = | 1.0 |
| Microcrystalline cellulose | 410.0 |
| Starch | 50.0 |
| Sodium starch glycolate | 15.0 |
| Magnesium stearate | 5.0 |
| | 481 |

| iii) Capsule | mg/capsule |
|---|---|
| Compound X = | 2.0 |
| Colloidal silicon dioxide | 1.5 |
| Lactose | 465.5 |
| Pregelatinized starch | 120.0 |
| Magnesium stearate | 3.0 |
| | 468 |

| (iv) Injection 1 (1 mg/ml) | mg/ml |
|---|---|
| Compound X = | 0.5 |
| Dibasic sodium phosphate | 12.0 |
| Monobasic sodium phosphate | 0.7 |
| Sodium chloride | 4.5 |
| 1.0N Sodium hydroxide solution (pH adjustment to 8.2-9) | q.s. |
| Water for injection | q.s. ad 1 mL |

| (v) Injection 1 (1 mg/ml) | mg/ml |
|---|---|
| Compound X = | 1 |
| Dibasic sodium phosphate | 12.0 |
| Monobasic sodium phosphate | 0.7 |
| Sodium chloride | 4.5 |
| 1.0N Sodium hydroxide solution (pH adjustment to 8.2-9.0) | q.s. |
| Water for injection | q.s. ad 1 mL |

| (vi) Injection 2 (10 mg/ml) | mg/ml |
|---|---|
| Compound X = | 2 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 8.2-9.0) | q.s. |
| Water for injection | q.s. ad 1 mL |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating cancer in a mammal, comprising administering to the mammal a compound of formula I:

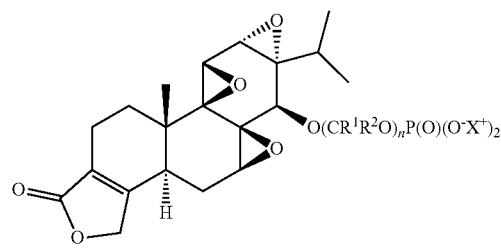

wherein:
  each $R^1$ is independently H, $(C_1-C_6)$alkyl, aryl$(C_1-C_6)$alkyl-, $(C_3-C_6)$cycloalkyl or aryl; and each $R^2$ is independently H, $(C_1-C_6)$alkyl, aryl$(C_1-C_6)$alkyl-, $(C_3-C_6)$cycloalkyl or aryl; or $R^1$ and $R^2$ together with the atom to which they are attached form a $(C_3-C_7)$cycloalkyl; wherein any alkyl or cycloalkyl of $R^1$ or $R^2$ may be optionally substituted with one or more groups selected from halo, $(C_1-C_6)$alkoxy and $NR^aR^b$ and wherein any aryl of $R^1$ or $R^2$ may be optionally substituted with one or more groups selected from halo, $(C_1-C_6)$alkyl, $(C_1-C_6)$alkoxy, $NR^aR^b$, nitro and cyano;

$R^a$ and $R^b$ are each independently selected from H, $(C_1-C_6)$alkyl, $(C_3-C_6)$cycloalkyl and aryl; or $R^a$ and $R^b$ together with the nitrogen to which they are attached form a pyrrolidino, piperidino, piperazino, azetidino, morpholino, or thiomorpholino;

n is 1, 2 or 3; and each X is H;

or a pharmaceutically acceptable salt thereof;

wherein the cancer is selected from pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer and lymphoma tumors.

2. The method of claim 1 wherein the compound of formula I is a compound of formula Ia:

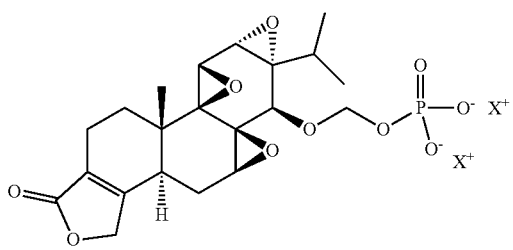

wherein $X^+$ is a pharmaceutically acceptable organic cation or inorganic cation.

3. The method of claim 1 wherein $R^1$ is H or $(C_1-C_6)$alkyl.
4. The method of claim 1 wherein $R^1$ is H.
5. The method of claim 1 wherein $R^1$ is $(C_1-C_6)$alkyl.
6. The method of claim 1 wherein $R^1$ is methyl or ethyl.
7. The method of claim 1 wherein $R^2$ is H or $(C_1-C_6)$alkyl.
8. The method of claim 1 wherein $R^2$ is H.
9. The method of claim 1 wherein each $X^+$ is H.
10. The method of claim 1 wherein each $X^+$ is lithium, sodium, potassium, magnesium, calcium, barium, zinc or aluminum.
11. The method of claim 1 wherein each $X^+$ is of the formula $HY^+$ wherein Y is ammonia, triethylamine, tromethamine, triethanolamine, ethylenediamine, glucamine, N-methylglucamine, glycine, lysine, ornithine, arginine, ethanolamine or choline.
12. The method of claim 1 wherein $X^+$ is selected from $Li^+$, $K^+$ and $Na^{30}$.
13. The method of claim 1 wherein each $X^+$ is $Na^+$.
14. The method of claim 1 wherein 14-O-phosphonooxymethyltriptolide disodium salt, 14-O-phosphonooxyethyltriptolide disodium salt or 14-O-phosphonooxypropyltriptolide disodium salt is administered.
15. The method of claim 1 wherein 14-O-phosphonooxymethyltriptolide disodium salt is administered.
16. A method for treating an HSP70-expressing cancer in a mammal, comprising administering to the mammal a compound of formula I:

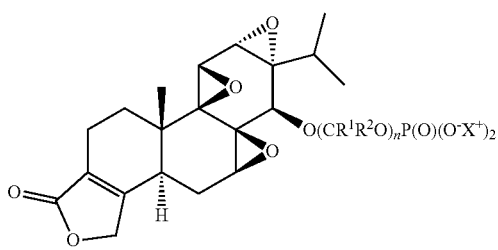

wherein:
each $R^1$ is independently H, $(C_1-C_6)$alkyl, aryl$(C_1-C_6)$alkyl-, $(C_3-C_6)$cycloalkyl or aryl; and each $R^2$ is independently H, $(C_1-C_6)$alkyl, aryl$(C_1-C_6)$alkyl-, $(C_3-C_6)$cycloalkyl or aryl; or $R^1$ and $R^2$ together with the atom to which they are attached form a $(C_3-C_7)$cycloalkyl; wherein any alkyl or cycloalkyl of $R^1$ or $R^2$ may be optionally substituted with one or more groups selected from halo, $(C_1-C_6)$alkoxy and $NR^aR^b$ and wherein any aryl of $R^1$ or $R^2$ may be optionally substituted with one or more groups selected from halo, $(C_1-C_6)$alkyl, $(C_1-C_6)$alkoxy, $NR^aR^b$, nitro and cyano;
$R^a$ and $R^b$ are each independently selected from H, $(C_1-C_6)$alkyl, $(C_3-C_6)$cycloalkyl and aryl; or $R^a$ and $R^b$ together with the nitrogen to which they are attached form a pyrrolidino, piperidino, piperazino, azetidino, morpholino, or thiomorpholino;
n is 1, 2 or 3; and
each X is H;
or a pharmaceutically acceptable salt thereof;
wherein the cancer is selected from pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer and lymphoma tumors.

17. The method of claim 1 wherein the cancer is pancreatic cancer, breast cancer, colon cancer, gastric cancer, liver cancer, neuroblastoma or glioblastoma.
18. The method of claim 16 wherein the cancer is pancreatic cancer, breast cancer, colon cancer, gastric cancer, liver cancer, neuroblastoma or glioblastoma.
19. The method of claim 18 wherein 14-O-phosphonooxymethyltriptolide disodium salt is administered.
20. A method for treating pancreatic cancer in a mammal, comprising administering to the mammal a compound of formula I:

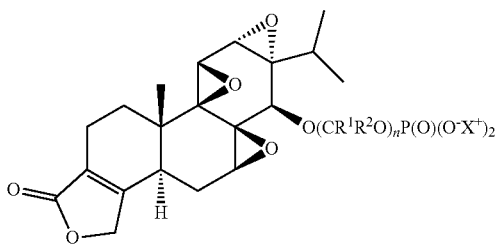

wherein:
each $R^1$ is independently H, $(C_1-C_6)$alkyl, aryl$(C_1-C_6)$alkyl-, $(C_3-C_6)$cycloalkyl or aryl; and each $R^2$ is independently H, $(C_1-C_6)$alkyl, aryl$(C_1-C_6)$alkyl-, $(C_3-C_6)$cycloalkyl or aryl; or $R^1$ and $R^2$ together with the atom to which they are attached form a $(C_3-C_7)$cycloalkyl; wherein any alkyl or cycloalkyl of $R^1$ or $R^2$ may be optionally substituted with one or more groups selected from halo, $(C_1-C_6)$alkoxy and $NR^aR^b$ and wherein any aryl of $R^1$ or $R^2$ may be optionally substituted with one or more groups selected from halo, $(C_1-C_6)$alkyl, $(C_1-C_6)$alkoxy, $NR^aR^b$, nitro and cyano;
$R^a$ and $R^b$ are each independently selected from H, $(C_1-C_6)$alkyl, $(C_3-C_6)$cycloalkyl and aryl; or $R^a$ and $R^b$ together with the nitrogen to which they are attached form a pyrrolidino, piperidino, piperazino, azetidino, morpholino, or thiomorpholino;
n is 1, 2 or 3; and
each X is H;
or a pharmaceutically acceptable salt thereof.

21. A method for treating pancreatic cancer in a mammal, comprising administering to the mammal 14-O-phosphonooxymethyltriptolide disodium salt.

* * * * *